(12) United States Patent
Girijavallabhan

(10) Patent No.: US 10,953,029 B2
(45) Date of Patent: Mar. 23, 2021

(54) 4'-SUBSTITUTED NUCLEOSIDE REVERSE TRANSCRIPTASE INHIBITORS AND PREPARATIONS THEREOF

(71) Applicant: Merck Sharp & Dohme Corp., Rahway, NJ (US)

(72) Inventor: Vinay M. Girijavallabhan, Whippany, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/761,742

(22) PCT Filed: Sep. 19, 2016

(86) PCT No.: PCT/US2016/052409
§ 371 (c)(1),
(2) Date: Mar. 20, 2018

(87) PCT Pub. No.: WO2017/053216
PCT Pub. Date: Mar. 30, 2017

(65) Prior Publication Data
US 2019/0022115 A1  Jan. 24, 2019

Related U.S. Application Data

(60) Provisional application No. 62/302,452, filed on Mar. 2, 2016, provisional application No. 62/222,304, filed on Sep. 23, 2015.

(51) Int. Cl.
| | | |
|---|---|---|
| C07H 19/14 | (2006.01) |
| A61K 31/7064 | (2006.01) |
| C07D 307/33 | (2006.01) |
| A61K 45/06 | (2006.01) |
| C07H 1/00 | (2006.01) |
| C07H 23/00 | (2006.01) |
| C07H 19/16 | (2006.01) |
| A61P 31/18 | (2006.01) |

(52) U.S. Cl.
CPC .......... *A61K 31/7064* (2013.01); *A61K 45/06* (2013.01); *A61P 31/18* (2018.01); *C07D 307/33* (2013.01); *C07H 1/00* (2013.01); *C07H 19/14* (2013.01); *C07H 19/16* (2013.01); *C07H 23/00* (2013.01)

(58) Field of Classification Search
None
See application file for complete search history.

(56) References Cited

U.S. PATENT DOCUMENTS

| | | | |
|---|---|---|---|
| 6,333,315 B1 | 12/2001 | Ohrui et al. |
| 6,403,568 B1 | 6/2002 | Ohrui et al. |
| 7,339,053 B2 | 3/2008 | Kohgo et al. |
| 7,625,877 B2 | 12/2009 | Kohgo et al. |
| 7,879,815 B2 | 2/2011 | MacCoss et al. |
| 8,039,614 B2 | 10/2011 | Kohgo et al. |
| 8,835,615 B2 | 9/2014 | Chang |
| 9,777,035 B2 * | 10/2017 | Girijavallabhan ........... A61K 31/7064 |
| 10,093,683 B2 | 10/2018 | Lim et al. |
| 2004/0229839 A1 | 11/2004 | Babu et al. |
| 2005/0020825 A1 * | 1/2005 | Storer ............. C07H 1/00 536/27.1 |
| 2005/0059632 A1 | 3/2005 | Storer et al. |
| 2010/0227833 A1 | 9/2010 | Yin et al. |
| 2010/0234584 A1 | 9/2010 | Chang |
| 2011/0171192 A1 | 7/2011 | Tominyama et al. |
| 2014/0309412 A1 | 10/2014 | Bhat et al. |
| 2015/0133395 A1 | 5/2015 | Clarke et al. |

FOREIGN PATENT DOCUMENTS

| | | |
|---|---|---|
| CN | 101177442 A | 5/2008 |
| EP | 1589026 A1 | 10/2005 |
| EP | 2177527 A1 | 4/2010 |

(Continued)

OTHER PUBLICATIONS

Wolff, Manfred E. "Burger's Medicinal Chemistry, 5ed, Part I", John Wiley & Sons, 1995, pp. 975-977. (Year: 1995).*

Banker, G.S. et al, "Modern Pharmaceutics, 3ed.", Marcel Dekker, New York, 1996, p. 596. (Year: 1996).*

Kageyama et al., Bioscience, Biotechnology, and Biochemistry, 2012, 76(6), 1219-1225. (Year: 2012).*

(Continued)

*Primary Examiner* — Traviss C McIntosh, III
(74) *Attorney, Agent, or Firm* — Carol S. Quagliato; John C. Todaro

(57) ABSTRACT

The present invention is directed to 4'-substituted nucleoside derivatives of Formula (I) and their use in the inhibition of HIV reverse transcriptase, the prophylaxis of infection by HIV, the treatment of infection by HIV, and the prophylaxis, treatment, and delay in the onset or progression of AIDS and/or ARC. The present invention also provides processes for the preparation of 4'-substituted nucleoside derivatives of Formula (I) and derivatives thereof.

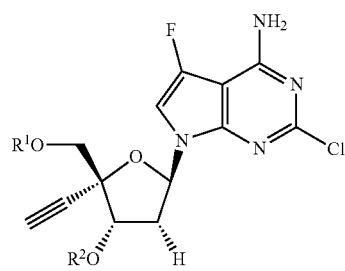

12 Claims, No Drawings

(56) References Cited

FOREIGN PATENT DOCUMENTS

| | | |
|---|---|---|
| KR | 20100102089 A | 9/2010 |
| WO | 1991010671 A1 | 7/1991 |
| WO | 1995021184 A1 | 8/1995 |
| WO | 1998016184 A2 | 4/1998 |
| WO | 2002100354 A1 | 12/2002 |
| WO | 2003061576 A2 | 7/2003 |
| WO | 2003099840 A1 | 12/2003 |
| WO | 2004106356 A1 | 12/2004 |
| WO | 2008048981 A2 | 4/2008 |
| WO | 2008082602 A2 | 7/2008 |
| WO | 2008089105 A2 | 7/2008 |
| WO | 2009009951 A1 | 1/2009 |
| WO | 2009067409 A1 | 5/2009 |
| WO | 2009132123 A1 | 10/2009 |
| WO | 2009132135 A1 | 10/2009 |
| WO | 2010002877 A2 | 1/2010 |
| WO | 20100002877 A2 | 1/2010 |
| WO | 2010026153 A1 | 3/2010 |
| WO | 2010027005 A1 | 3/2010 |
| WO | 2010036407 A2 | 4/2010 |
| WO | 2010075517 A2 | 7/2010 |
| WO | 2010075549 A2 | 7/2010 |
| WO | 2010084115 A2 | 7/2010 |
| WO | 2010108140 A1 | 9/2010 |
| WO | 2011005860 A2 | 1/2011 |
| WO | 2012012776 A1 | 1/2012 |
| WO | 2012037038 A1 | 3/2012 |
| WO | 2013114780 A1 | 8/2013 |
| WO | 2013138236 A1 | 9/2013 |
| WO | 2015069939 A1 | 5/2015 |
| WO | 2015148746 A1 | 10/2015 |

OTHER PUBLICATIONS

Beaumont, K., et al,, "Design Of Ester Prodrugs To Enhance Oral Absorption of Poorly Permeable Compounds: Challenges To The Discovery Scientist", Current Drug Metabolism, 2003, pp. 461-485, vol. 4.

Bobeck, et al.,, "Advances In Nucleoside Monophosphate Prodrugs As Anti-HCV Agents", Antiviral Therapy, 2010, pp. 935-950, vol. 15.

Chemical Encyclopedia under the editorship of Knunyants, I.L., 1990, vol. 2, Sovietswkaya enciklopediya Publisher, p. 167.

Cristalli, G., et al, "Adenosine Deaminase Inhibitors. Synthesis And Biological Activity Of Deaza Analogues Of Erythro-9-(2-Hydroxy-3-Nonyl)Adenine", J. Med. Chem., 1988, pp. 390-393, vol. 31.

Danilova, G.A., Efficient Synthesis of (S)-5-Hydroxymethy1-5(H)-Furan-2-One from D-Mannitol, Tetrahedron Letters, 1986, 2489-2490, vol. 27, No. 22.

Desai, M., et al.,, "Antiretroviral Drugs: Critical Issues And Recent Advances", Indian J. Pharmacol., 2012, pp. 288-298, vol. 44, No. 3.

Erion, M., "Liver-Targeted Drug Delivery Using HepDirect Prodrugs", Metabsis Therapeutics, Inc., 2008, pp. 7-12, 17th International Symposium on Microsomes and drug Oxidations, Saratoga Springs (NY, USA), US.

Furman, et al.,, "Nucleoside Analog Inhibitors Of Hepatitis C Viral Replication: Recent Advances, Challenges And Trends", Future Medicinal Chemistry, 2009, pp. 1429-1452, vol. 1.

Gupta, M., et al, "Adenosine Deaminase In Nucleoside Synthesis. A Review", Collect. Czech. Chem. Commun., 2006, pp. 769-787, vol. 71, No. 6.

Hale, et al, "Phosphorylated Morpholine Acetal Human Neurokinin-1 Receptor Antagonists As Water-Soluble Prodrugs", J. Med. Chem, 2000, pp. 1234-1241, vol. 43.

Higuchi, T., et al., "Pro-drugs as NovelDelivery Systems", A.C.S. Symposium Series, 1987, 14, pp. 1-6.

International Search Report and Written Opinion for PCT/US2016/052409, dated Mar. 31, 2017; 12 pages.

International Search Report and Written Opinion of the International Searching Authority, PCT/CN2014/074294—International Filing Date Mar. 28, 2014.

International Search Report and Written Opinion of the International Searching Authority, PCT/US2015/022621—International Filing Date Mar. 3, 2015.

Kageyama, M., et al, "Enantioselective Total Synthesis Of The Potent Anti-HIV Nucleoside EFdA", Organic Letters, 2011, pp. 5264-5266, vol. 13, No. 19.

Kazuhiro Haraguchi, et al, "Synthesis Of 4'-Ethynyl-2'-Deoxy-4'-Thioribonucleosides And Discovery Of A Highly Potent And Less Toxic NRTI", ACS Medicinal Chemistry Letters, 2011, pp. 692-697, vol. 2, No. 9, WO.

Kesisoglou, F., et al, "Nanosizing—Oral Formulation Development and Biopharmaceutical Evaluation", Advance Drug Delivery Reviews, 2007, pp. 631-644, vol. 59, US.

Kirby, K., et al, "Effects of Substitutions at the 4' and 2 Positions on the Bioactivity of 4'-Ethyny1-2-Fluoro-2'-Deoxyadenosine", Antimicrobial Agents and Chemotherapy, 2013, pp. 6254-6264, vol. 57, No. 12.

Kodama, et al, "4'-Ethynyl Nucleoside Analogs: Potent Inhibitors Of Multidrug-Resistant Human Immunodeficiency Virus Variants In Vitro", Antimicrobial Agents and Chemotherapy, American Society for Microbiology, 2001, pp. 1539-1546, vol. 45, No. 5, WO.

Kohgo, S., et al.,, "Design, Efficient Synthesis, and Anti-HIV Activity of 4'-C-Cyano- and 4'-C-Ethynyl-2'-Deoxy Purine Nucleosides", Nucleosides, Nucleotides & Nucleic Acids, 2004, pp. 671-690, vol. 23, No. 4.

Kohgo, S., et al.,, "Synthesis of 4'-C-Ethynyl and 4'-C-Cyano Purine Nucleosides from Natural Nucleosides and Their Anti-HIV Activity", Nucleosides, Nucleotides & Nucleic Acids, 2003, pp. 887-889, vol. 22, Nos. 5-8.

Krogsgaard-Larsen, P., et al, "Design and Applcation of Prodrugs", Drug Design and Discovery, 2002, pp. 461-485, 4d Edition, vol. 4, US.

Larsen, C.S., et al,, "Design And Application Of Prodrugs", Textbook of Drug Design and Discovery, 3rd Ed, 2002, pp. 410-458, Chapter 14, US.

Marongiu, M., et al, "Enhancement Of The Anti-HIV-1 Activity Of ddAdo By Coformycin, EHNA and Deaza-EHNA Derivatives", Microbiologica, 1995, pp. 359-370, vol. 18, No. 4.

Mehellou, Y., "Phosphoramidate Prodrugs Deliver with Potency Against Hepatitis C Virus", Chem. Med. Chem., 2010, pp. 1841-1842, vol. 5.

Obara, T., et al, "New Neplanocin Analogues. 7. Synthesis and Antiviral Activity of 2-Halo Derivatives of Neplanocin A1", Journal of Medicial Chemistry, 1996, pp. 3847-3852, vol. 39, No. 19.

Ohrui, H., "4'-C-Ethynyl-2'-Deoxynucleosides", Modified Nucleosides: In Biochemistry, Biotechnology and Medicine, 2008, pp. 425-431.

Ohrui, H., "Development Of Modified Nucleosides That Have Supremely High Anti-HIV Activity And Now Toxicity And Prevent The Emergence Of Resistant HIV mUTANTS", Proc. Jpn. Acad., Ser., 2011, pp. 53-65, vol. 87, No. 3.

Serajuddin, A., et al.,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.

Shuto, S., et al, "New Neplanocin Analogues. IV. 2-Fluoroneplanocin A: An Adenosine Deaminase-Resistant Equivalent of Neplanocin A1", Chem.Pharm. Bull., 1994, pp. 1688-1690, vol. 42, No. 8.

Supplementary European Search Report and Opinion for 16849385.6 dated May 10, 2019; 11 pages.

* cited by examiner

4'-SUBSTITUTED NUCLEOSIDE REVERSE TRANSCRIPTASE INHIBITORS AND PREPARATIONS THEREOF

RELATED APPLICATIONS

This application is a 35 U.S.C. § 371 filing from International Application No. PCT/US16/052409, filed Sep. 19, 2016, which claims priority to U.S. Provisional Application No. 62/302,452, filed Mar. 2, 2016, and U.S. Provisional Application No. 62/222,304, filed Sep. 23, 2015. Each of the aforementioned applications to which this application claims priority is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are nucleoside RT inhibitors (NRTI) such as 3'-azido-3'-deoxythymidine (AZT), 2',3'-dideoxyinosine (ddI), 2',3'-dideoxycytidine (ddC), d4T, 3TC, abacavir, emtricitabine, and tenofovir disoproxil fumarate, as well as non-nucleoside RT inhibitors (nNRTI) such as nevirapine, delavirdine, and efavirenz.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of anti-retrovirals to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a continuing need for new RT inhibitors that are effective against mutant HIV strains.

In addition, new routes for preparing nucleoside RT inhibitors are needed, particularly for preparing multi-kilogram quantities of drug substance required to support animal toxicology studies and subsequent human clinical trials. For instance, several routes to the 4'-substituted nucleoside derivative, 4'-ethynyl-2-fluoro-2'-deoxyadenosine (EFdA)

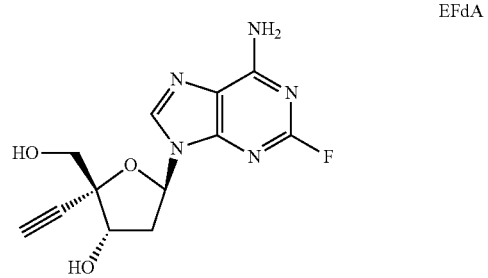 [SMILES: C#C[C@]1(CO)O[C@@H](n2cnc3c(N)nc(F)nc32)C[C@@H]1O]

EFdA have appeared in the literature, including two reports in Organic Letters published in 2011 and 2015 (Kuwahara et al., Org. Lett. 2011, 13, 5264 and Kuwahara/Ohrui et al., Org. Lett. 2015, 17, 828). EFdA has been reported to provide potent antiviral activity against wild-type and multi-drug resistant HIV-1 strains. The published routes to EFdA have drawbacks with respect to production of multi-kilogram quantities of drug substance required for further studies. In particular, some of the published routes use the chiral starting material (R)-glyceraldehyde acetonide, which is not readily available at large scale and is also prone to stereochemical erosion. In addition, the published routes lack a sufficient number of crystalline intermediates to enable purity control without resort to chromatographic purification. The published routes also use hazardous or impractical reagents, and synthetic methods that are not optimized for large-scale implementation due to the reagents' toxicities or the methods' hazards.

SUMMARY OF THE INVENTION

The present invention is directed to 4'-substituted nucleoside derivatives and their use in the inhibition of HIV reverse transcriptase, the prophylaxis of infection by HIV, the treatment of infection by HIV, and the prophylaxis, treatment, and delay in the onset or progression of AIDS and/or ARC.

The present invention also provides a process for the preparation of 4'-ethynyl-2'-deoxyribonucleosides, such as EFdA and the compounds having structural Formula I. In addition, the invention provides certain synthetic intermediates which are useful in preparing 4'-ethynyl-2'-deoxyribonucleosides.

DETAILED DESCRIPTION OF THE INVENTION

The present invention is directed to compounds having structural Formula I:

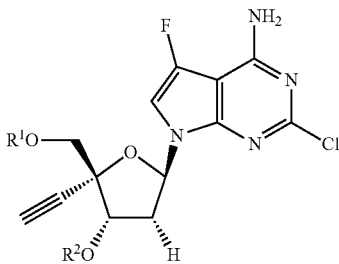

or a pharmaceutically acceptable salt thereof, wherein:
$R^1$ is —H, —C(O)$R^3$, —C(O)O$R^3$, —C(O)N($R^3$)$_2$,

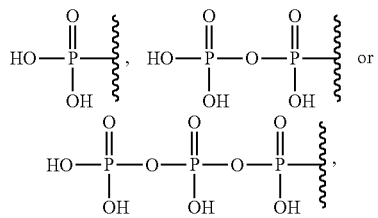

or a pro-drug modification of the mono-, di- or triphosphate; and
$R^2$ is —H, —C(O)$R^4$, —C(O)O$R^4$ or —C(O)N($R^4$)$_2$;
$R^3$ and $R^4$ are each independently selected at each occurrence from —H, —$C_1$-$C_6$ alkyl, —$C_1$-$C_6$ haloalkyl, —($C_1$-$C_3$ alkylene)$_m$-($C_3$-$C_7$ cycloalkyl), —($C_1$-$C_3$ alkylene)$_m$-(aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein each of said —$C_1$-$C_6$ alkyl, said —$C_3$-$C_7$ cycloalkyl group, said aryl group, said 4 to 7-membered heterocycloalkyl group, said 5- or 6-membered monocyclic heteroaryl group or said 9- or 10-membered bicyclic heteroaryl group is unsubstituted or substituted with $R^5$;
m is an integer selected from 0 (zero) or 1; and
$R^5$ represents from one to five substituent groups, each independently selected from —$C_1$-$C_6$alkyl, —$C_2$-$C_6$ alkenyl, —$C_2$-$C_6$ alkynyl, —$C_1$-$C_6$ haloalkyl, aryl or a 5-6-member heteroaryl.

In Embodiment A of this invention are compounds of Formula I, or a pharmaceutically acceptable salt thereof, wherein $R^1$ is —H, —C(O)$R^3$, —C(O)O$R^3$, —C(O)N($R^3$)$_2$, or a pro-drug modification of one of the following mono-, di- or triphosphate moieties:

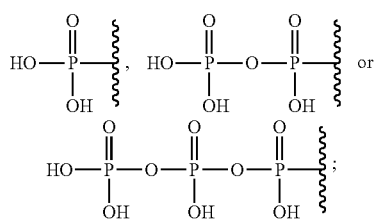

and $R^2$ is —H, —C(O)$R^4$, —C(O)O$R^4$ or —C(O)N($R^4$)$_2$.
In Embodiment B of this invention are compounds of Formula I, or a pharmaceutically acceptable salt thereof, wherein $R^1$ is —H, —C(O)$R^3$, —C(O)O$R^3$, or —C(O)N($R^3$)$_2$; and $R^2$ is —H, —C(O)$R^4$, —C(O)O$R^4$ or —C(O)N($R^4$)$_2$.

In Embodiment C of this invention are compounds of Formula I or Embodiment A or B, or a pharmaceutically acceptable salt thereof, wherein at least one of $R^1$ or $R^2$ is —H.

In Embodiment D of this invention are compounds of Formula I wherein $R^1$ is

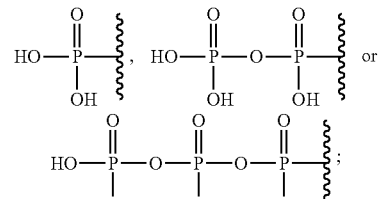

and $R^2$ is —H.

Examples of compounds of Formula I of this invention are the following Compound 1 or Compound 2, or a pharmaceutically acceptable salt thereof:

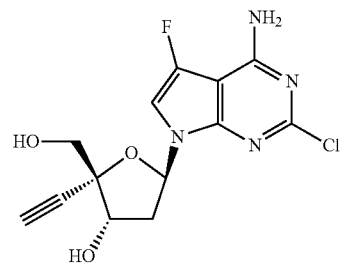

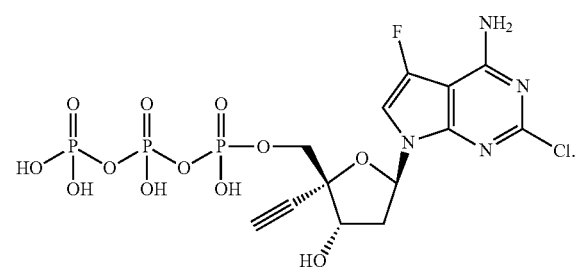

Reference to the compounds of this invention as those of a specific formula or embodiment, e.g., Formula I, or Embodiments A, B or C thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise. The present invention includes each of the Examples described herein, and pharmaceutically acceptable salts thereof. The invention also encompasses pharmaceutical compositions comprising an effective amount of a compound of the invention or a pharmaceutically acceptable salt thereof, and a pharmaceutically acceptable carrier.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" (or "$C_1$-$C_4$ alkyl") refers to n-, iso-, sec- and t-butyl, n- and iso-propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_{2-6}$ alkenyl" (or "$C_2$-$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl).

The term "alkynyl" refers to a monovalent straight or branched chain aliphatic hydrocarbon radical containing one carbon-carbon triple bond and having a number of carbon atoms in the specified range. Thus, for example, "$C_{2-6}$ alkynyl" (or "$C_2$-$C_6$ alkynyl") refers to all of the hexynyl and pentynyl isomers as well as 1-butynyl, 2-butynyl, 3-butynyl, 1-propynyl, 2-propynyl, and ethynyl.

The term "alkylene" refers to any divalent linear or branched chain aliphatic hydrocarbon radical having a number of carbon atoms in the specified range. Thus, for example, "—$C_1$-$C_3$ alkylene-" refers to any of the $C_1$ to $C_3$ linear or branched alkylenes. A particular class of alkylenes includes —$(CH_2)_{1-3}$—, —$(CH_2)_{2-3}$—, —$(CH_2)_{1-2}$—, —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_3$-$C_7$ cycloalkyl" (or "$C_3$-$C_7$ cycloalkyl") refers to cyclopropyl, cyclobutyl, cyclopentyl, cyclohexyl, and cycloheptyl.

A particular class of interest for compounds of Formula I and embodiments thereof is $C_3$-$C_6$ cycloalkyl. "Heterocycloalkyl" refers to a cycloalkyl ring wherein one or two of the carbon atoms in the ring are replaced by a heteroatom independently selected from N, O and S.

The term "halogen" (or "halo") refers to fluorine, chlorine, bromine and iodine (alternatively referred to as fluoro, chloro, bromo, and iodo). A particular class of interest for compounds of Formula I and embodiments thereof is each of fluoro of chloro.

The term "haloalkyl" refers to an alkyl group as defined above in which one or more of the hydrogen atoms have been replaced with halo (i.e., —F, —Cl, —Br and/or —I). Thus, for example, "$C_1$-$C_6$ haloalkyl" refers to a $C_1$ to $C_6$ linear or branched alkyl group as defined above with one or more halo substituents.

The term "C(O)" refers to carbonyl.

The term "aryl" (or "$C_6$-$C_{10}$ aryl") refers to (i) phenyl, or (ii) 9- or 10-membered bicyclic, fused carbocyclic ring systems in which at least one ring is aromatic. Suitable aryls include, for example, phenyl, naphthyl, tetrahydronaphthyl (tetralinyl), or indenyl. In a particular class of compounds of Formula I and embodiments thereof, aryl is phenyl or naphthyl, and more particularly aryl is phenyl.

The term "heteroaryl" refers to (i) a 5- or 6-membered heteroaromatic ring containing from 1 to 4 heteroatoms independently selected from N, O and S, wherein each N is optionally in the form of an oxide to the extent chemically possible, (ii) a 9- or 10-membered bicyclic fused ring system, wherein the fused ring system contains from 1 to 6 heteroatoms independently selected from N, O and S, wherein each ring in the fused ring system contains zero, one, or more than one heteroatom, and at least one ring is aromatic, and each N is optionally in the form of an oxide to the extent chemically possible, and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl (e.g., benzo-1,3-dioxolyl:

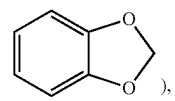), benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl (i.e.,

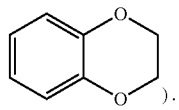).

It is understood that the specific rings and ring systems suitable for use in the present invention are not limited to those listed in the preceding paragraphs. These rings and ring systems are merely representative. Unless expressly stated to the contrary in a particular context, any of the various cyclic rings and ring systems described herein may be attached to the rest of the compound at any ring atom (i.e., any carbon atom or any heteroatom) provided that the attachment is chemically allowed and a stable compound results.

When any variable occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heteroaryl group described as containing from "1 to 4 heteroatoms" is intended to include as aspects thereof, heteroaromatic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. "Optionally" substituted means a chemical moeity can be unsubstituted or substituted with the noted substituents.

As would be recognized by one of ordinary skill in the art, certain of the compounds of the present invention can exist as tautomers. All tautomeric forms of these compounds, whether isolated individually or in mixtures, are within the scope of the present invention. For example, in instances where an —OH substituent is permitted on a heteroaromatic ring and keto-enol tautomerism is possible, it is understood that the substituent might in fact be present, in whole or in part, in the oxo (=O) form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments.

The compounds of Formula I may have one or more chiral (asymmetric) centers. Centers of asymmetry that are present in the compounds of Formula I can all independently of one another have (R) or (5) configuration, except for the chiral centers depicted in structural Formula I as having a specific stereoconfiguration. The present invention encompasses all such stereoisomeric forms of the compounds of Formula I.

The invention includes all possible enantiomers and diastereomers and mixtures of two or more stereoisomers of compounds of Formula I when chiral centers are possible in $R^3$, $R^4$ and/or $R^5$, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Examples and descriptions herein using appropriate isotopically-enriched reagents and/or intermediates.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof). When the compounds of Formula I contain one or more acidic or basic groups the invention also includes the corresponding pharmaceutically acceptable salts. Thus, the compounds of Formula I which contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Another embodiment of the present invention is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. A substantially pure compound can be either a substantially pure mixture of stereoisomers or a substantially pure individual diastereomer or enantiomer.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

It is understood that a compound of Formula I (or any embodiment thereof and pharmaceutically acceptable salts thereof) may be converted intracellularly/in vivo by one or more mechanisms (e.g., enzyme-catalyzed chemical reactions) to the corresponding nucleoside 5' triphosphate, i.e., wherein $R^1$ is —P(O)(OH)—O—P(O)(OH)—O—P(O)(OH)$_2$) and $R^2$ is H. While not wishing to be bound by any particular theory, the nucleoside 5'triphosphate is generally understood to be responsible for inhibiting the HIV RT enzyme and for the resulting antiviral activity after administration of the compound of Formula I to a subject. For example, Compound 2 described herein is a nucleoside 5'triphosphate analog of Compound 1.

Accordingly, prodrugs of the compounds of the invention are contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" herein means a compound (e.g., a drug precursor), which may be in the form of a pharmaceutically acceptable salt, that is transformed intracellularly/in vivo to provide a 4'-substituted Nucleoside Derivative which is an inhibitor of HIV reverse transcriptase. A nucleoside 5'triphosphate is an example of a 4'-substituted Nucleoside Derivative. The in vivo transformation may occur by various mechanisms, e.g., an enzyme-catalyzed chemical reaction, a metabolic chemical reaction, and/or a spontaneous chemical reaction (e.g., solvolysis), such as, for example, through hydrolysis in blood. This invention encompasses any prodrugs which convert, due to intracellular/in vivo conversion, to a 4'-substituted Nucleoside Derivative of a compound of Formula I which is an inhibitor of HIV reverse transcriptase. For example, 4'-substituted Nucleoside Derivatives of Formula I include, but are not limited to, compounds of Formula I wherein:
a) $R^1$ is —P(O)(OH)—O—P(O)(OH)—O—P(O)(OH)$_2$; or
b) $R^1$ is —P(O)(OH)—O—P(O)(OH)—O—P(O)(OH)$_2$ and $R^2$ is —H.

Prodrugs of compounds of Formula I can exhibit enhanced solubility, absorption, and/or lipophilicity compared to the compounds per se, thereby resulting in increased bioavailability and efficacy. When the compound of Formula I contains a hydroxy group at the 5' and/or 3' positions, (i.e., when $R^1$ is —H, and/or $R^2$ is —H), the prodrug can be a derivative of the hydroxy group such as when $R^1$=—C(O)R$^3$, —C(O)OR$^3$ or —C(O)N(R$^3$)$_2$, and/or $R^2$=—C(O)R$^4$, —C(O)OR$^4$ or —C(O)N(R$^4$)$_2$.

In Formula I, $R^1$ also includes pro-drug modification of the mono-, di- or triphosphate. This prodrug modification can be a derivative of one or more of the hydroxy groups on a mono-, di- or triphosphate moiety, such as an ester (—OC(O)R), a carbonate ester (—OC(O)OR), an ether (—OR), a phosphate ester (—O—P(=O)(OC(O)R)$_2$), or a mono-phosphate prodrug such as a phosphoramidate (which can be converted in vivo to the corresponding nucleoside monophosphate). The pro-drug modification of the mono-, di- or triphosphate also includes, but is not limited to, 5'-alcohol-derived prodrugs such as —P(O)(—O—C$_1$-C$_6$alkyl)$_2$; —P(O)(—NH-(α-aminoacyl group))(-O-aryl) known as "McGuigan" type prodrugs; —P(O)(—O—(C$_1$-C$_6$ alkylene)-(S-acyl)(-NH-arylalkyl); S-acyl-2-thioethyl (SATE) prodrugs; or a cyclic phosphate ester that forms a bridge between two ribose hydroxyl groups, such as:

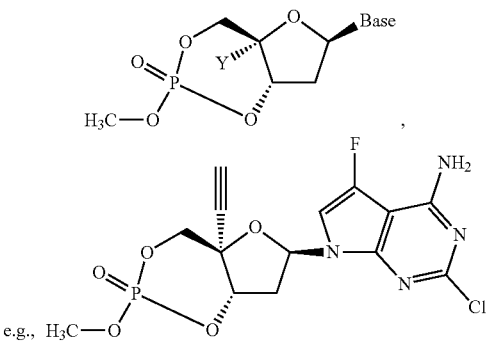

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

As further examples of prodrugs, if a compound of Formula I contains an alcohol functional group at any of the above-described positions in the compound, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino (C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

The compounds of Formula I also contains an amine functional group. A prodrug of a compound of Formula I can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino $(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aryl (e.g., benzyl), aryloxyalkyl (for example, phenoxymethyl), aryl (e.g., phenyl optionally substituted with, for example, halogen, $C_{1-4}$alkyl, —O— $(C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

If a 4'-substituted deoxyribose derivative contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Other examples include the following: when the compound of Formula I contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. Conventional procedures for the selection and preparation of suitable prodrug derivatives are described, for example, in Design of Prodrugs, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties.

Accordingly, the compounds within the structural Formula I, embodiments and specific compounds described and claimed herein encompass salts, any possible stereoisomers and tautomers, physical forms (e.g., amorphous and crystalline forms), solvate and hydrate forms thereof and any combination of these forms, as well as the salts thereof, pro-drug forms thereof which include any combination of stereoisomer, tautomer, solvate, hydrate, salt and/or physical forms of said pro-drugs, where such forms are possible unless specified otherwise.

The invention also encompasses methods for the treatment or prophylaxis of infection by HIV, for the inhibition of HIV reverse transcriptase, or for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the treatment or prophylaxis of infection by HIV, for the inhibition of HIV reverse transcriptase, or for the treatment, prophylaxis, or delay in the onset of AIDS in a subject in need thereof. The invention also encompasses a pharmaceutical composition comprising an effective amount of a compound of the invention, or a pharmaceutically acceptable salt thereof, and a pharmaceutically acceptable carrier and further comprising an effective amount of an additional anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Compounds of Embodiment A, B or C each form a subset of the compounds included in Formula I. Any description above or which follows that refers to a compound of Formula I also applies to a compound of each of Embodiment A, B or C and any embodiments thereof.

Other embodiments of the present invention include the following:

(a) A pharmaceutical composition comprising an effective amount of a compound of Formula I as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a prodrug or pharmaceutically acceptable salt thereof, and a pharmaceutically acceptable carrier.

(c) The pharmaceutical composition of (a) or (b), further comprising an effective amount of one or more an anti-HIV agents selected from the group consisting of HIV antiviral agents, immunomodulators, and anti-infective agents.

(d) The pharmaceutical composition of (c), wherein the anti-HIV agent is selected from one or more of an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(e) A combination which is (i) a compound of Formula I as defined above, or a prodrug or pharmaceutically acceptable salt thereof, and (ii) an anti-HIV agent selected from the group consisting of HIV antiviral agents, immunomodulators, and anti-infective agents; wherein the compound and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(g) A method for the inhibition of HIV reverse transcriptase in a subject in need thereof which comprises administering to the subject an effective amount of a compound of Formula I or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I or a prodrug or pharmaceutically acceptable salt thereof.

(i) The method of (h), wherein the compound of Formula I is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(j) A method for the prophylaxis, treatment or delay in the onset or progression of AIDS in a subject in need thereof which comprises administering to the subject an effective amount of a compound of Formula I or a prodrug or pharmaceutically acceptable salt thereof.

(k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments described above. In all of these embodiments, the compound may optionally be used in the form of a prodrug or pharmaceutically acceptable salt or pharmaceutically acceptable salt of a prodrug.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I or its prodrug and/or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors. The compounds of Formula I may also be useful agents against HIV-2.

The term "administration" and variants thereof (e.g., "administering" a compound) in reference to a compound of Formula I means providing the compound to the individual in need of treatment or prophylaxis and includes both self-administration and administration to the patient by another person. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are "pharmaceutically acceptable" ingredients, which means the ingredients must be compatible with each other and not deleterious to the recipient thereof.

The term "subject" as used herein refers to an animal, preferably a mammal, most preferably a human, who has been the object of treatment, observation or experiment.

The term "effective amount" as used herein means an amount sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS, delaying the onset of AIDS, and/or slowing progression of AIDS in a patient. Another embodiment of "effective amount" is a "prophylactically effective amount" which is an amount of the compound that is effective for prophylaxis of HIV infection or prophylaxis of AIDS in a patient. It is understood that an effective amount can simultaneously be both a therapeutically effective amount, e.g., for treatment of HIV infection, and a prophylactically effective amount, e.g., for prevention or reduction of risk for developing AIDS. When the compound of Formula I is administered as a salt, reference to an amount of the compound is to the free form (i.e., the non-salt form) of the compound.

In the method of the present invention (i.e., inhibiting HIV reverse transcriptase, treating or prophylaxis of HIV infection, inhibiting HIV replication, treating or prophylaxis of AIDS, delaying the onset of AIDS, or delaying or slowing progression of AIDS), the compounds of this invention, optionally in the form of a salt, can be administered by means that produce contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques, or by implantable device), by inhalation spray, or rectally, in the form of a unit dosage of a pharmaceutical composition containing an effective amount of the compound and conventional non-toxic pharmaceutically acceptable carriers, adjuvants and vehicles, any of which administration methods can be provided as a single dose, once-daily, or less frequently such as once weekly or once monthly, twice yearly or once yearly in, for example but not limited to, the dosage ranges and amounts described below. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18th edition, edited by A. R. Gennaro, Mack Publishing Co., 1990 and in *Remington—The Science and Practice of Pharmacy*, 22nd Edition, published by Pharmaceutical Press and Philadelphia College of Pharmacy at University of the Sciences, 2012, ISBN 978 0 85711-062-6 and prior editions.

Formulations of compounds described by Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are well known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I, and pharmaceutically acceptable salts thereof, can be useful for inhibiting HIV reverse transcriptase and for inhibiting HIV replication in vitro and in vivo. More particularly, the compounds of Formula I can be useful for inhibiting the polymerase function of HIV-1 reverse transcriptase. The testing of Compound 1 in the assay set forth in the RT Polymerase Assay below, illustrates the ability of compounds of the invention to inhibit the RNA-dependent DNA polymerase activity of HIV-1 reverse transcriptase. The compounds of Formula I may also be useful agents against HIV-2.

The compounds of Formula I can be administered in a dosage range of 0.001 to 1000 mg/kg of mammal (e.g., human) body weight per day, or at other time intervals as appropriate, in a single dose or in divided doses. One example of a dosage range is 0.01 to 500 mg/kg body weight per day, or at other time intervals as appropriate, administered orally or via other routes of administration in a single dose or in divided doses. Another example of a dosage range is 0.1 to 100 mg/kg body weight per day, or at other time intervals as appropriate, administered orally or via other routes of administration in single or divided doses. For oral (e.g., tablets or capsules) or other routes of administration, the compositions can be provided containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. Compounds of the invention can be administered as a single dose, once-daily, or less frequently such as once weekly, once monthly, twice yearly or once yearly in, for example but not limited to, the dosage ranges and amounts noted above. Furthermore, the compound may be formulated for immediate or modified release such as extended or controlled release.

As noted above, the present invention is also directed to use of a compound of Formula I with one or more anti-HIV agents. An "anti-HIV agent" is any agent which is directly or indirectly effective in the inhibition of HIV, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| Tenofovir alafenamide fumarate (GS-7340) | nRTI |
| tipranavir, Aptivus ® | PI |
| vicriviroc | EI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition.

In another aspect, the present invention provides a process for preparation of the compound of Formula (IA).

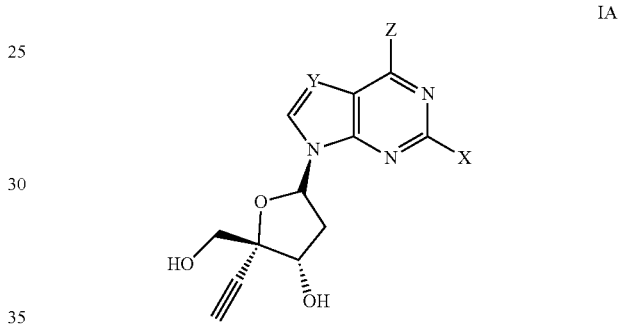

wherein X is H, F, Cl, or Br;

Y is N, C(H), C(F), C(Cl), C(Br), or C(CH$_3$); and

Z is NH$_2$. Thus, in embodiment in no. 1, the present invention provides a process comprising:

(a.) coupling sugar

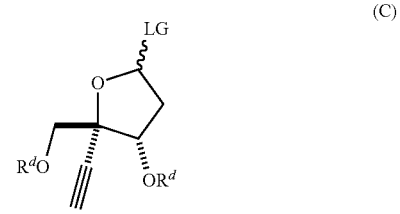

with nucleobase

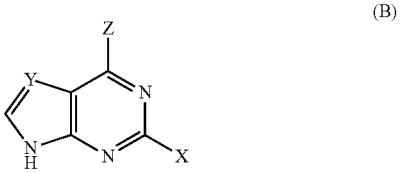

to provide protected nucleoside

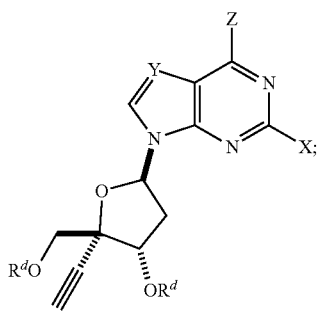
(A)

and
(b.) converting the protected nucleoside (A) to the compound of Formula (IA);
wherein
$Z^1$ is Cl, N(H)PG, or N(PG)$_2$,
$R^d$ is
(i) a group of the formula

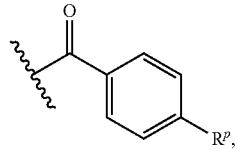

wherein $R^p$ is $C_1$-$C_3$ alkyl, $C_1$-$C_3$ alkoxy, halo, CF$_3$, or N(CH$_3$)$_2$;
(ii) —Si(R$^s$)$_3$; or
(iii) —C(O)C$_1$-C$_3$ alkyl; or
(iv) —C(O)CH$_2$N(H)C(O)CH$_3$;
each $R^s$ is independently $C_1$-$C_6$ alkyl; unsubstituted phenyl; phenyl substituted by one to three $C_1$-$C_3$ alkyl, halo, or $C_1$-$C_3$ alkoxy;
LG is OAc, OBz, halo, or —O—C$_2$-C$_8$ alkenyl; and
PG is an amino protecting group.

The amino protecting group can be a carbamate-based protecting group such as —C(O)OR$^s$ (e.g., Boc, CBz); a silyl protecting group such as —Si(R$^s$)$_3$, (e.g., (—Si(CH$_3$)$_3$, —Si(CH$_3$)$_2$(C(CH$_3$)$_3$)); or an amide protecting group such as —C(O)R$^s$ (e.g., —C(O)CH$_3$, —C(O)Ph).

In embodiment no. 2, the present invention provides a process as set forth in embodiment no. 1, wherein $R^d$ is 4-methylbenzoyl (Tol):

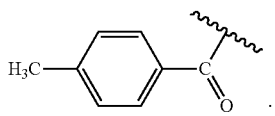 [SMILES: *C(=O)c1ccc(C)cc1]

In embodiment no. 3, the present invention provides a process as set forth in embodiment no. 2, wherein in the compound of Formula (IA), X is F, Y is N, and Z is NH$_2$.

In embodiment no. 4, the present invention provides a process as set forth in embodiment no. 3, wherein in step (a.),
in the sugar (C), LG is —OAc or —O(CH$_2$)$_3$C(H)=CH$_2$; and
in the protected nucleoside (A), X is F, Y is N, and $Z^1$ is N(H)PG.

In embodiment no. 5, the present invention provides a process as set forth in embodiment no. 4, wherein LG is —OAc in the sugar (C); and
$Z^1$ is N(H)Si(R$^s$)$_3$ in the protected nucleoside.

In embodiment no. 6, the present invention provides a process as set forth in embodiment no. 5, wherein in step (a) said coupling is conducted in the presence of a Lewis or Brønsted acid in an aprotic solvent to provide nucleoside (A). Suitable Lewis acids for the coupling include TMSOTf, TiCl$_4$, and SnCl$_4$. Suitable Brønsted acids include, for example, trifluoromethanesulfonic acid.

In embodiment no. 7, the present invention provides a process as set forth in embodiment no. 6, wherein the Lewis or Brønsted acid is TMSOTf.

In embodiment no. 8, the present invention provides a process as set forth in embodiment no. 6 or 7, wherein the aprotic solvent is acetonitrile.

In embodiment no. 9, the present invention provides a process as set forth in any one of embodiment nos. 6-8, wherein the coupling is conducted at a temperature from 60 to 85° C.

In embodiment no. 10, the present invention provides a process as set forth in embodiment no. 9, wherein the volume ratio of the aprotic solvent to sugar (C) is at least 10. For instance, volume ratio of the aprotic solvent to sugar (C) is 20 to 40.

In embodiment no. 11, the present invention provides a process as set forth in any one of embodiment nos. 6-10, wherein step (a.) further comprises isolating the protected nucleoside (A) by crystallizing the protected nucleoside (A) from a mixture containing the aprotic solvent and the nucleobase (B); and separating the protected nucleoside (A) from the mixture.

In embodiment no. 12, the present invention provides a process as set forth in any one of embodiment nos. 4-11, wherein $Z^1$ is —N(H)Si(CH$_3$)$_3$.

In embodiment no. 13, the present invention provides a process as set forth in embodiment no. 12, wherein the nucleobase (B) is prepared by reacting N,O-bis(trimethylsilyl)acetamide with 2-fluoroadenine.

In embodiment no. 14, the present invention provides a process as set forth in any one of embodiment nos. 5-13, wherein converting in step (b) comprises reacting the protected nucleoside (A) with an alkali metal $C_1$-$C_3$ alkoxide.

In embodiment no. 15, the present invention provides a process as set forth in embodiment no. 14, wherein the alkali metal $C_1$-$C_3$ alkoxide is sodium methoxide. In specific embodiments, the conversion is conducted with 3 to 10 mol. % NaOMe to the protected nucleoside (A).

In embodiment no. 16, the present invention provides a process as set forth in any one of embodiment nos. 5-15, wherein the sugar (C) is prepared by reacting lactol

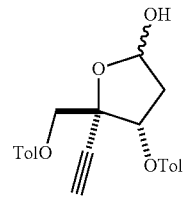
(10A)

with acetic anhydride.

In embodiment no. 17, the present invention provides a process as set forth in embodiment no. 4, wherein LG is —O(CH$_2$)$_3$C(H)=CH$_2$ in the sugar (C); and Z$^1$ is N(H)C(O)—OR$^s$ and X is F or Cl in the nucleobase (B) and in the protected nucleoside (A). In specific embodiments, Z$^1$ is N(H)C(O)—OR$^s$ and X is F in the nucleobase (B) and in the protected nucleoside (A).

In embodiment no. 18, the present invention provides a process as set forth in embodiment no. 17, wherein in step (a) said coupling is conducted by treating sugar (C) with a activating agent in the presence of nucleobase (B) in an aprotic solvent. Typically, the activating agent is iodine, bromine, N-iodosuccinimide, N-bromosuccinimide, Balarenga's reagent (Py$_2$I), or diiodo-dimethylhydantoin. For instance in one embodiment, the activating agent is iodine.

In embodiment no. 19, the present invention provides a process as set forth in embodiment no. 18, wherein the aprotic solvent is acetonitrile, propionitrile, ethyl acetate, dichloromethane, THF, toluene, 1,4-dioxane, an acetonitrile-THF mixture, an acetonitrile-dichloromethane mixture, an acetonitrile-toluene mixture or an acetonitrile-N-methylpyrrolidone mixture.

In embodiment no. 20, the present invention provides a process as set forth in embodiment no. 18 or 19, wherein the coupling is conducted at a temperature from –78 to 45° C. For instance, the coupling can be conducted at –40 to 10° C.

In embodiment no. 21, the present invention provides a process as set forth in any one of embodiment nos. 17-20, wherein Z$^1$ is N(H)C(O)—OC(CH$_3$)$_3$.

In embodiment no. 22, the present invention provides a process as set forth in any one of embodiment nos. 17-21, wherein converting in step (b) comprises treating the protected nucleoside (A) with an alkali metal C$_1$-C$_3$ alkoxide (e.g., sodium methoxide) and with a strong acid, in separate steps. The strong acid can be, for instance, trifluoroacetic acid or a mineral acid. The term "mineral acid" refers to a common inorganic acid, such as hydrochloric acid or sulphuric acid. In some embodiments, the protected nucleoside (A) is treated with the strong acid first and then with the alkali metal C$_1$-C$_3$ alkoxide. In other embodiments, the protected nucleoside (A) is treated first with the alkali metal C$_1$-C$_3$ alkoxide, and then with the strong acid.

In embodiment no. 23, the present invention provides a process as set forth in any one of embodiment nos. 17-22, wherein the sugar (C) is prepared by reacting lactol

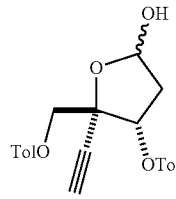

(10A)

with pent-4-en-1-ol to provide the sugar

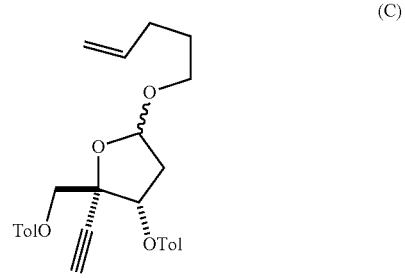

(C)

wherein LG is —O—(CH$_2$)$_3$CH=CH$_3$ (herein referred as sugar (C3).

In embodiment no. 24, the present invention provides a process as set forth in embodiment no. 23, wherein the reacting further comprises reacting lactol (10A) with acetic anhydride and pent-4-en-1-ol to provide the sugar (C).

In embodiment no. 25, the present invention provides a process as set forth in embodiment no. 2, wherein in the compound of Formula (IA), X is Cl, Y is C(F) or C(H), and Z is NH$_2$.

In embodiment no. 26, the present invention provides a process as set forth in embodiment no. 25, wherein in step (a.), in the sugar (C), LG is —Cl (referred to as sugar (C2)); and X is Cl, Y is C(F), and Z$^1$ is Cl in the nucleobase (B) and in the protected nucleoside (A).

In embodiment no. 27, the present invention provides a process as set forth in embodiment no. 25, wherein in step (a.) said coupling is conducted by treating nucleobase (B) with an alkali metal base in an aprotic solvent to provide a alkali metal salt of the nucleobase (B); and reacting the alkali metal salt of the nucleobase (B) with sugar (C) to provide the protected nucleoside (A).

Suitable alkali metal bases for treatment of the nucleobase (B) include, for example, NaHMDS, NaH, KHMDS, and LDA. In embodiment no. 28, the alkali metal base is NaHMDS.

In embodiment no. 29, the present invention provides a process as set forth in any one of embodiment nos. 25-28, wherein converting in step (b) comprises reacting the protected nucleoside (A) with ammonia. For example, the conversion can be conducted in a solution of ammonia in a C$_1$-C$_3$ alcohol, such as methanol.

In embodiment no. 30, the present invention provides a process as set forth in any one of embodiment nos. 26-29, wherein the sugar (C2) is prepared by reacting lactol

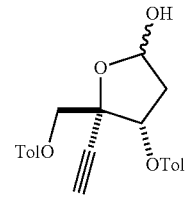

(10A)

with acetic anhydride to provide the sugar

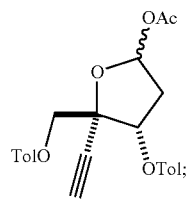
(C1)

and reacting the sugar (C1) with hydrochloric acid to provide the sugar (C2)

In embodiment no. 31, the present invention provides a process as set forth in any one of embodiment nos. 2-30, wherein the sugar (C) is prepared by
reducing lactone

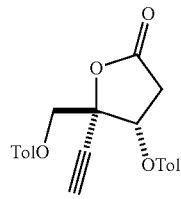
(10)

with a selective reducing agent to provide lactol

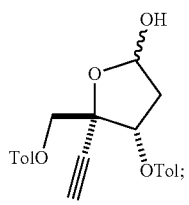
(10A)

and
converting lactol (10A) to the sugar (C).

In embodiment no. 32, the present invention provides a process as set forth in embodiment no. 31, wherein the selective reducing agent is sodium bis(2-methoxyethoxy) aluminum hydride.

In embodiment no. 33, the present invention provides a process as set forth in embodiment no. 31, wherein the lactone (10) is prepared by:
reacting dioxolane

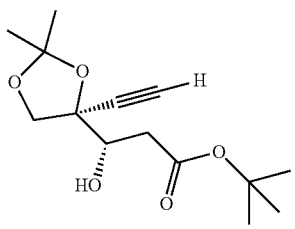
(9)

with an acid to provide a deprotected intermediate; and acylating the deprotected intermediate with a p-methylbenzoylating agent to provide the lactone (10).

The acylation of the deprotected intermediate described in embodiment no. 33 can be performed using a number of methods known to those skilled in the art of organic chemistry, for instance, by using p-methylbenzoylating agents such as anhydrides of p-methylbenzoic acid or p-methylbenzoyl chloride. In embodiment no. 34, the p-methylbenzoylating agent is p-methylbenzoyl chloride.

In embodiment no. 35, the present invention provides a process as set forth in embodiment no. 33, wherein the process further comprises isolating lactone (10) by crystallizing lactone (10). Suitable solvents for crystallizing and isolating lactone (10) include a mixture of pyridine:water and a mixture of isopropyl acetate:heptane.

In embodiment no. 36, the present invention provides a process as set forth in embodiment no. 33, wherein the deprotected intermediate is

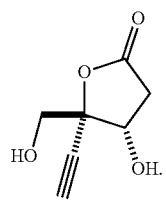
(10D)

In embodiment no. 37, the present invention provides a process as set forth in any one of embodiment nos. 33-36, wherein the dioxolane (9) is prepared by
reacting TIPS intermediate

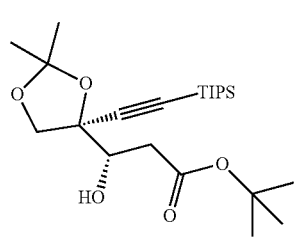
(8)

with a fluoride agent to provide the dioxolane (9). Suitable fluoride agents include, for example, tetraalkylammonium fluoride, potassium fluoride, and hydrofluoric acid. In embodiment no. 38, the fluoride agent is tetrabutylammonium fluoride.

In embodiment no. 39, the present invention provides a process as set forth in embodiment no. 37, wherein the TIPS intermediate (8) is prepared by reducing ketone ester

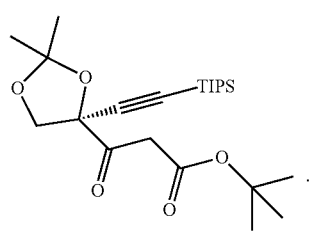
(7)

In embodiment no. 40, the reduction set forth in embodiment no. 39 is performed by asymmetric transfer hydrogenation of the ketone ester (7) with formic acid/triethylamine in the presence of a chiral catalyst. Suitable chiral catalysts for the hydrogenation include, for example, ruthenium-based catalysts containing chiral ligands, such as DENEB™, available from Takasago International Corporation, Tokyo, Japan. In embodiment no. 41, the chiral catalyst is RuCl—(S,S)-Ts-DENEB™.

In embodiment no. 42, the present invention provides a process as set forth in any one of embodiment nos. 39-41, wherein the ketone ester (7) is prepared by converting alcohol

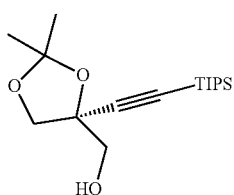

(4)

to the ketone ester (7).

In embodiment no. 43, the present invention provides a process as set forth in embodiment no. 42, wherein the conversion of alcohol (4) to ketone ester (7) comprises:

(i.) oxidizing alcohol (4) to provide carboxylic acid

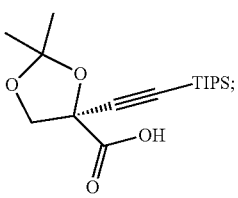

(5)

(ii.) esterifying the carboxylic acid (5) provide methyl ester

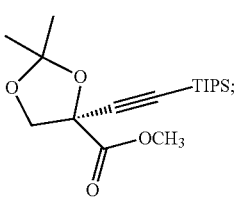

(6)

(iii.) reacting an alkali metal enolate of tert-butyl acetate with methyl ester (6) to provide ketone ester (7).

Suitable oxidation conditions to oxidize alcohol (4) and provide carboxylic acid (5) include a two-step oxidation process or a direct oxidation process. Two-step oxidation processes include oxidation of the alcohol moiety to an aldehyde, such as by using Dess-Martin periodinane or Parikh-Doering oxidation (DMSO, $SO_3 \cdot pyr$, triethylamine), followed by oxidation of the aldehyde to the carboxylic acid, using for example, Pinnick oxidation ($NaClO_2$, tert-butanol, $NaH_2PO_4$). Direct oxidation is a one-step oxidation process of the alcohol (4) to the carboxylic acid (5). Typically this one-step oxidation process includes treatment of alcohol (4) with 2,2,6,6-tetrmethylpiperidin-1-oxyl (TEMPO), NaOCl, $NaOCl_2$ at a pH of about 4.

The esterification of the carboxylic acid (5) to provide the methyl ester (6) can be performed in a number of ways. The carboxylic acid (5) can be treated with a base which is suitable for forming the carboxylate anion (e.g., DBU), and a methylating agent such as methyl iodide or dimethylsulfate. Alternatively, the carboxylic acid (5) can be activated with a carbodiimide agent such as N,N'-carbonyldiimidazole, and then quenched with methanol to provide the methyl ester (6).

Formation of the alkali metal enolate of tert-butyl acetate can be conducted with with an alkali metal base such as LDA or NaHMDS. The enolate the alkali metal enolate is reacted with the methyl ester (6) to form the ketone ester (7).

In some embodiments, further improvement of the purity of the acid (5) may be desired. Accordingly, in embodiment no. 44, the present invention provides a process as set forth in embodiment no. 43, wherein the process further comprises:

(i.) treating carboxylic acid (5) with an amine to form a salt of (5) with the amine

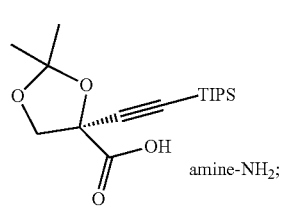

(amine-5)

(ii.) isolating the salt (amine-5); and (iii.) reacting the salt (amine-5) with an acid (e.g., citric acid) to provide purified carboxylic acid (5).

In some embodiments, the amines used to treat carboxylic acid (5) can be an achiral amine such as tert-butylamine. In other embodiments, the acid (5) is treated with a chiral amine such as phenylmethylamine, phenylethylamine, 1-amino-2-indanol, 1-(1-napthyl)ethylamine, 1-(2-napthyl)ethylamine, cinchonine, or norephredine. In embodiment no. 45, the carboxylic acid (5) is treated with (1R,2S)-(+)-cis-1-amino-2-indanol.

In embodiment no. 46, the present invention provides a process as set forth in any one of embodiment nos. 43-45, wherein the alcohol (4) is prepared by:

(i.) reacting diol

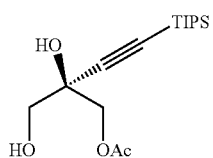

(3)

with an acetonide-forming agent and an acid to form acetonide

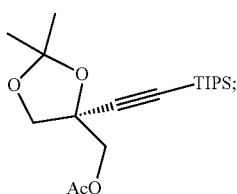

(3a)

and (ii.) treating acetonide (3a) with an alkali metal $C_1$-$C_3$ alkoxide to form the alcohol (4).

In embodiment no. 47, the acetonide-forming reacted with diol (3) in embodiment no. 46 is 2,2-dimethoxypropane, 2-methoxypropene or acetone. In embodiment no. 48, the acetonide-forming agent is 2,2-dimethoxypropane.

In embodiment no. 49, the alkali metal $C_1$-$C_3$ alkoxide used to form the alcohol (4) in embodiment no. 46, 47 or 48 is sodium methoxide.

In embodiment no. 50, the present invention provides a process as set forth in any one of embodiment nos. 46-49, wherein the diol (3) is prepared by contacting diacetoxy alcohol

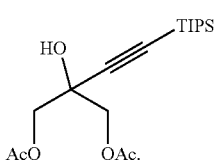

(I-2)

with a lipase.

In embodiment no. 51, the lipase contacted with diacetoxy alcohol (I-2) is *Candida antarctica* lipase A.

In embodiment no. 52, the present invention provides a process as set forth in any one of embodiment nos. 50 and 51, wherein the diacetoxy alcohol (I-2) is prepared by adding lithiated alkyne adduct

(1A)

to diacetoxyacetone

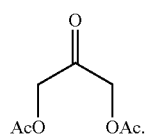

(I-1)

In another aspect, the present invention provides processes for the preparation of certain synthetic intermediates useful in the preparation of the compound of the Formula (IA). Thus, in embodiment no. 53, the present invention provides a process for the preparation of the lactone

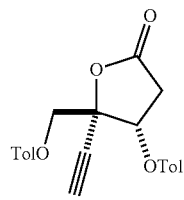

(10)

using the conditions set forth in any one of embodiment nos. 33-52. In embodiment no. 54 the present invention provides a process for the preparation of the lactone

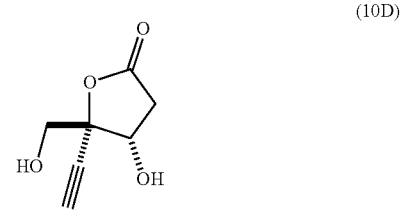

(10D)

using the conditions set forth in any one of embodiment nos. 33 and 36-52.

In embodiment no. 55, the present invention provides a process for preparation of the protected nucleoside

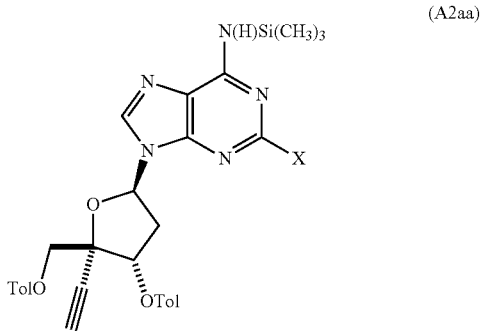

(A2aa)

wherein X is H, F, Cl or Br, using the conditions set forth in any one of embodiment nos. 5-13, 16 and 31-52. In a class of this process embodiment, the protected nucleoside (A2aa) is

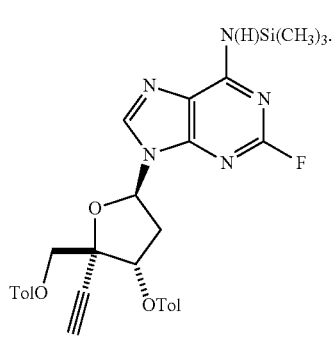

(A2a)

In embodiment no. 56, the present invention provides a process for preparation of the protected nucleoside

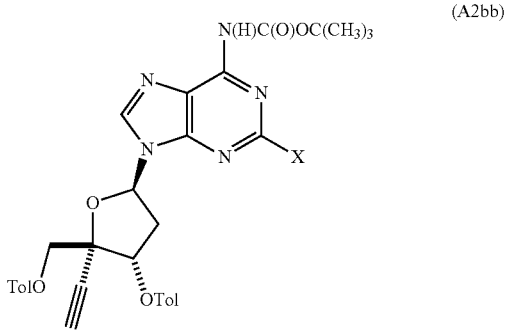

(A2bb)

wherein X is H, F, Cl or Br, using the conditions set forth in any one of embodiment nos. 17-24 and 31-52. In a class of this process embodiment, the protected nucleoside (A2bb) is

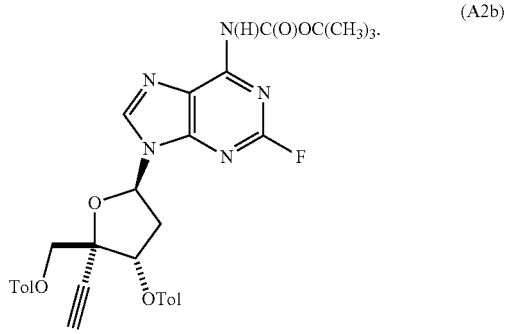

(A2b)

In embodiment no. 57, the present invention provides a process for the preparation of the protected nucleoside

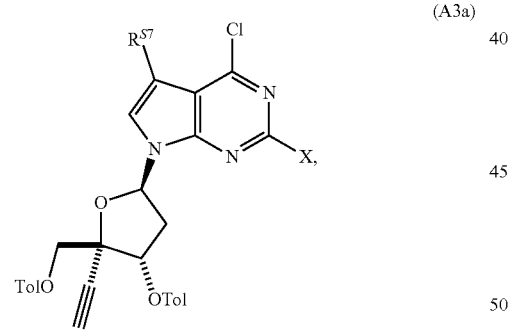

(A3a)

wherein X is H, F, Cl, or Br and $R^{S7}$ is H, F, Cl, Br, or $CH_3$ using the conditions set forth in any one of embodiment nos. 25-52. In a particular class of this process embodiment, X is Cl and $R^{S7}$ is F. In another particular class of this process embodiment, X is Cl and $R^{S7}$ is H.

In another aspect, the presentation invention provides synthetic intermediates useful in the preparation of the compound of Formula (IA). Thus, in embodiment no. 58, the present invention provides the protected nucleoside (A2aa), (A2bb), (A2a), (A2b), or (A3a).

In embodiment no. 59, the present invention provides the protected nucleoside (A2aa).

In embodiment no. 60, the present invention provides the protected nucleoside (A2b).

In embodiment no. 61, the present invention provides the protected nucleoside (A3a) wherein X is H, F, Cl, or Br and $R^{S7}$ is H, F, Cl, Br, or $CH_3$. In a class of this embodiment, X is Cl and $R^{S7}$ is F in the protected nucleoside (A3a). In another class of this embodiment, In a class of this embodiment, X is Cl and $R^{S7}$ is H.

In embodiment no. 62, the present invention provides the lactone

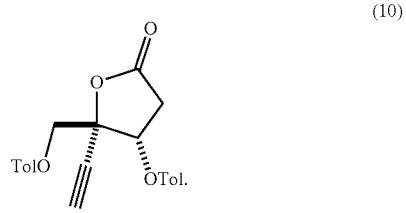

(10)

In embodiment no. 63, the present invention provides the lactone

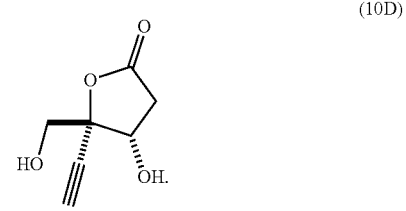

(10D)

In embodiment no. 64, the present invention provides the sugar

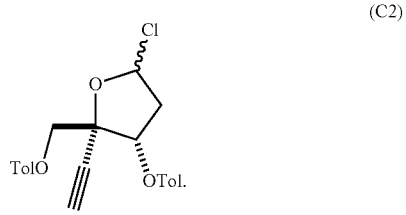

(C2)

In embodiment no. 65, the present invention provides the sugar

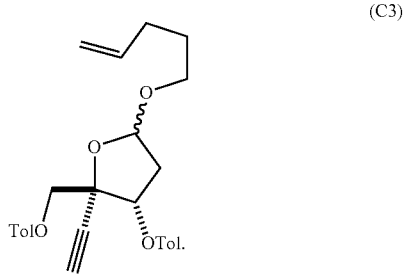

(C3)

Abbreviations and acronyms employed herein include the following:

| | |
|---|---|
| ACN = acetonitrile | NHS = normal human serum |
| AcOH = acetic acid; Ac = acyl; | NovoCor AD L = Lipase from Candida sp. |
| Ac₂O = acetic anhydride | recombinant, expressed in Aspergillus oryzae |
| ADA = adenosine deaminase | NMR = nuclear magnetic resonance |
| Boc = tert-butyloxycarbonyl | QTof = Quadrupole time of flight |
| BTMSA = bis-trimethylsilylacetamide | NTP = nucleoside triphosphate |
| DMF = N,N-dimethylformamide | dNTP = 2'-deoxy nucleoside triphosphate |
| BzCl = benzoyl chloride | pet. ether = petroleum ether |
| DCM = dichloromethane | Ppm, ppm = parts per million |
| DME = 1,2-dimethoxyethane | PPTS = 4-toluenesulfonic acid |
| DMSO = dimethylsulfoxide | r.t. = room temperature |
| EtOAc = ethyl acetate | RT = reverse transcriptase |
| Ecosorb C-941 = activated carbon | TBAF = tetrabutylammonium fluoride |
| EGTA = ethylene glycol tetraacetic acid | TEAB = triethylammonium bromide |
| Et₃N = triethylamine | TEMPO = 2,2,6,6-tetramethyl-1-piperidinyloxy |
| L = liter | THF = tetrahydrofuran |
| LDA = lithium diisopropylamide | TIPS = triisopropylsilyl |
| Me = methyl, Et = Ethyl, Pr = propyl, Bu = Butyl, Bz = benzoyl | TFA = trifluoroacetic acid |
| MeOH = methanol | TLC = thin layer chromatography |
| mL or ml = milliliter | TMS = trimethysilyl |
| mol = moles; M = molar | TMSOTf = trimethylsilyl trifluoromethanesulfonate |
| mmol = millimoles | Tol = p-methylbenzoyl |
| MTBE = methyl tert-butyl ether | |
| NaHMDS = sodium hexamethyldisilazide | TS-DENEB = N-[(1S,2S)-1,2-Diphenyl-2-(2-(4-methylbenzyloxy)ethylamino)-ethyl]-4-methylbenzene sulfonamide(chloro)ruthenium(II) |
| KHMDS—potassium hexamethyldisilazide | |
| CBz = benzyloxy carbonyl | DBU = 1,8-Diazabicyclo[5.4.0]undec-7-ene |

Compounds of the invention can be prepared by methods well known in the art of organic chemistry. See, for example, J. March, 'Advanced Organic Chemistry' 6th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 4th Edition, John Wiley and Sons. The protective groups are optionally removed at a convenient subsequent stage using methods well known in the art.

The compounds of Formula I can be readily prepared according to the following reaction schemes and examples, or modifications thereof, using readily available starting materials and reagents. In these reactions, it is also possible to make use of variants which are themselves known to those of ordinary skill in this art, but are not mentioned in greater detail.

Furthermore, other methods for preparing compounds of the invention will be readily apparent to the person of ordinary skill in the art in light of the following reaction schemes and examples. Unless otherwise indicated, all variables are as defined above.

-continued

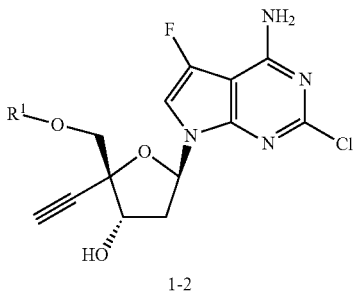

1-2

Compound 1 can be selectively reacted at the 5'-OH when treated with chlorides of type R¹—Cl in the presence of a base such as triethylamine to produce compounds of type 1-2.

Scheme 1

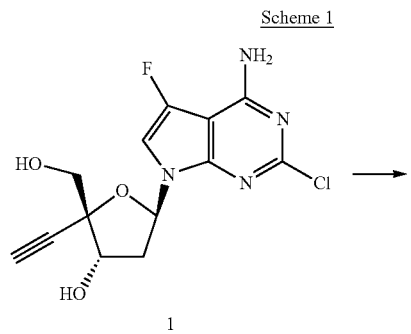

1

Scheme 2

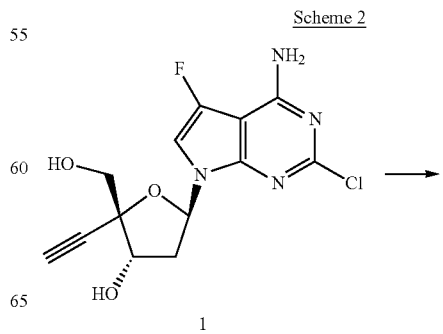

1

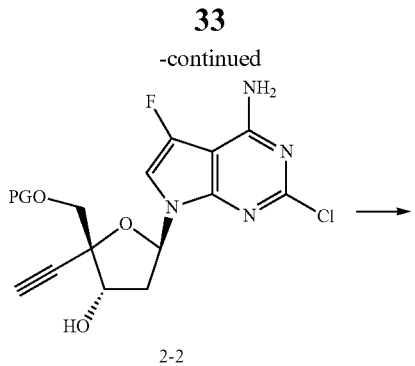

2-2

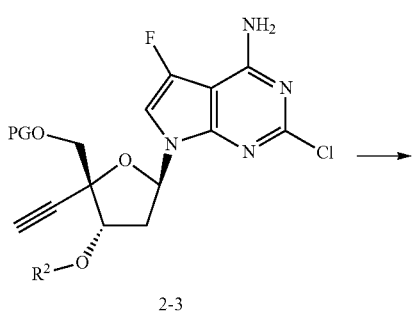

2-3

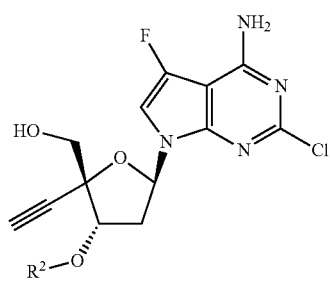

2-4

Compound 1 can be selectively protected with a 5'-OH protecting group (PG) to provide intermediate 2-2. Reaction of 2-2 with chlorides of type $R^2$—Cl in the presence of a base such as triethylamine to produce intermediate 2-3. Removal of the protecting group at the 5'-OH can provide compounds of type 2-4.

Scheme 3

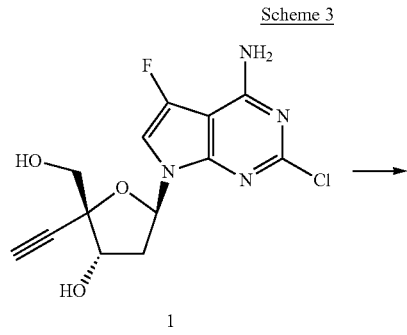

1

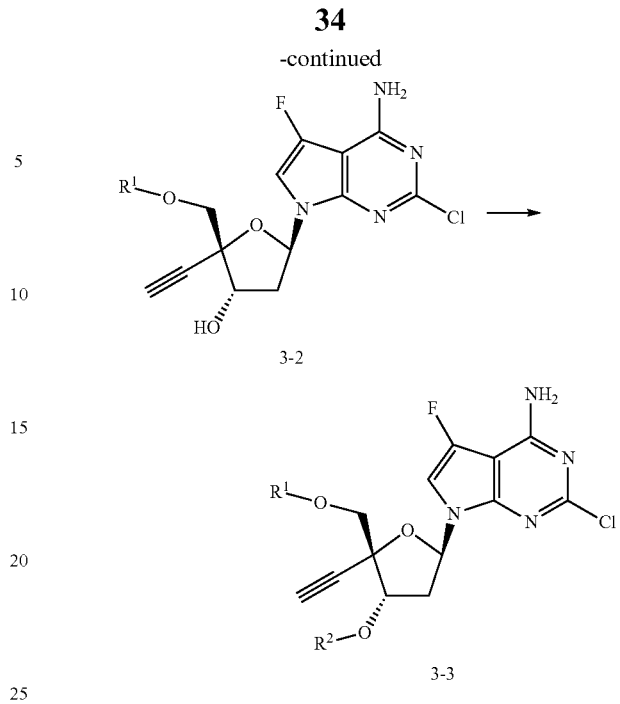

3-2

3-3

Compound 1 can be treated with chlorides of type $R^1$—Cl in the presence of a base such as triethylamine to produce intermediate 3-2. Intermediate 3-2 can be treated with chlorides of type $R^2$—Cl in presence of a base such as triethylamine to produce compounds of type 3-3.

Scheme 4 shows one embodiment of the process of the present invention, wherein the lactol 10A is prepared. As compared to the published procedures which disclose preparation of 4-ethynyl-2-deoxysugar coupling partner suitable for preparing EFdA, such as M. Kageyama et al., *Biosci. Biotechnol. Biochem.*, 76(6) 1219-1225 (2012), the process depicted in Scheme 4 utilizes a more readily available starting material, and is able to be performed at larger scales without chromatography.

Scheme 4

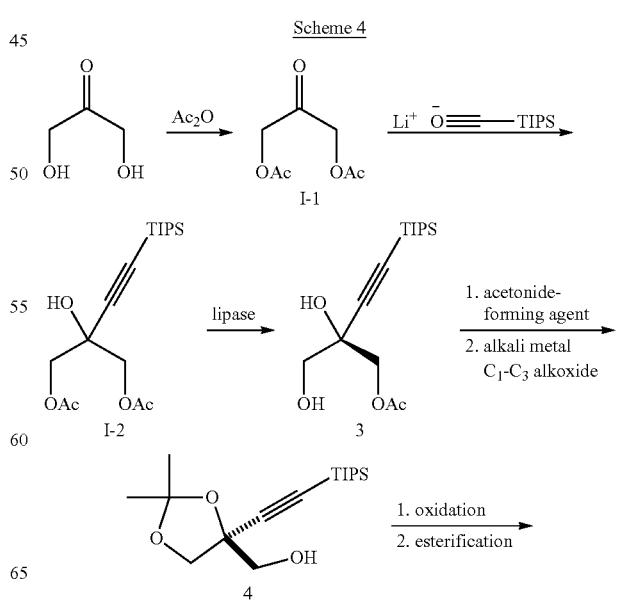

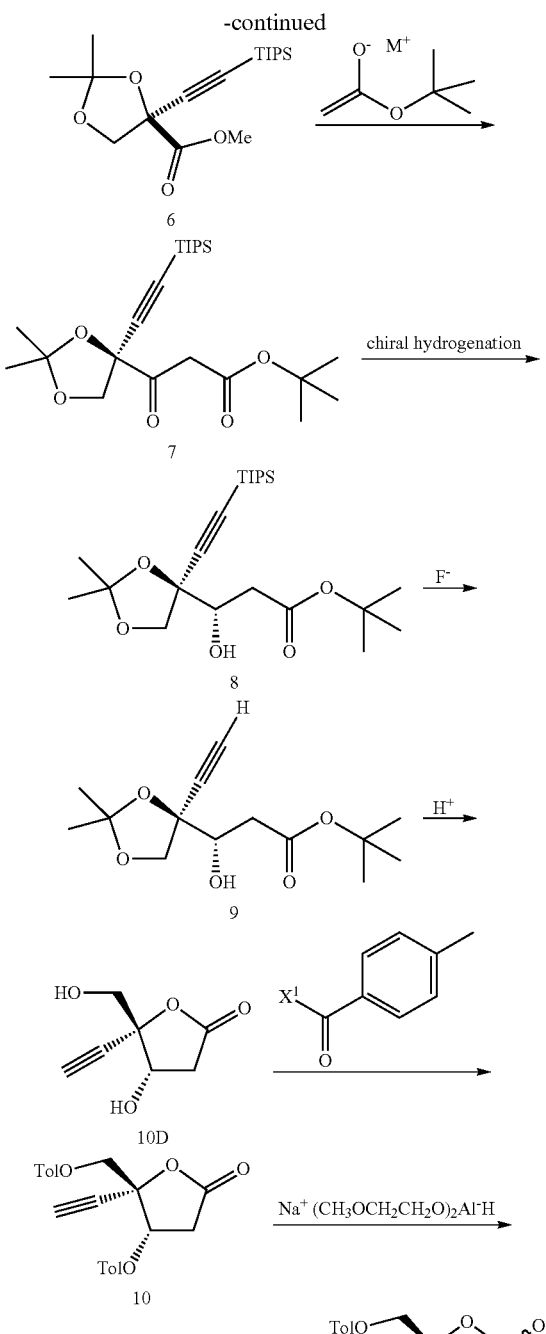

2,2-dimethoxypropane, acetone, or 2-methoxypropene and an acid such as pyridinium p-toluenesulfonate; followed by treating the intermediate acetonide with an alkali metal $C_1$-$C_3$ alkoxide such as sodium methoxide to remove the acetate group. Those of skill in the art will recognize that alternative ketal forming agents, such as diethyl ketal, cyclopentyl ketal and cyclohexyl ketal can be used in place of acetonide forming agents, to form similarly ketal-protected synthetic intermediates.

Formation of the ketone ester (7) from alcohol (4) occurs by oxidation of the alcohol (4) with an oxidation agent followed by esterification of the resultant carboxylic acid (5); and then condensation of the ester with an alkali metal enolate of tert-butyl acetate. In one embodiment, the oxidation conditions used include the reagents 2,2,6,6-tetramethylpiperidin-1-yl)oxyl (TEMPO), NaOCl, $NaOCl_2$ with a buffer system having a pH of about 4. Other suitable oxidizing systems include Dess-Martin periodinane, (diacetoxy)iodobenzene (DAIB), and Parikh-Doering oxidation (DMSO, $SO_3$.pyridine, triethylamine). The carboxylic acid (5) is esterified to prepare the methyl ester (6) by using dimethylsulfate and a base, or by using methanol and a carbodiimide-coupling agent such as N,N'-carbonyldiimidazole.

Optionally, the purity of the carboxylic acid (5) can be improved by forming a salt of the carboxylic acid with an amine, such as a chiral amine, isolation of the amine salt, followed by treatment with an acid to break the salt.

The ketone ester (7) is reduced, such as under asymmetric transfer hydrogenation conditions, to provide the TIPS intermediate (8). Suitable chiral catalysts include ruthenium-based catalysts with chiral ligands such as DENEB™ from Takasago International Corporation, Tokyo, Japan with a reducing agent such as formic acid/triethylamine. The triisopropylsilane group is removed from the TIPS intermediate (8) by treatment with a fluoride agent, such as potassium fluoride or tetrabutylammonium fluoride, to provide the dioxolane (9).

Deprotection and lactonization under acidic conditions (e.g., HCl) provides the lactone (10D) which can be isolated as a solid. The lactone (10D) is acylated with p-methylbenzoylating agent (p-methyl-Ph-C(O)$X^1$ in Scheme 4, wherein $X^1$ is a leaving group) such as p-methylbenzoyl chloride to provide lactone (10). The lactone (10) is reduced with a selective reducing agent, such as sodium bis(2-methoxyethoxy)aluminum hydride, to provide the lactol (10A).

As shown in Scheme 4, dihydroxyacetone is acetylated with acetic anhydride to provide diacetoxyacetone (I-1). A lithium adduct of ethynyltriisopropylsilane is added to diacetoxy acetone (I-1) to yield the diacetoxy alcohol (I-2). Treatment of the diacetoxy alcohol with a lipase (such as *Candida antartica* lipase A) provides enantiomerically enriched diol (3). The enzymatic hydrolysis selectively yields the R-diol with a percent enantiomeric excess (% ee) of greater than 90%, such as 92-96% ee.

Conversion of diol (3) to the alcohol (4) occurs by first treating diol (3) with an acetonide forming agent such as

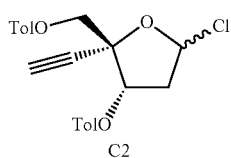

Scheme 5 shows embodiments of the process, wherein the lactol is converted to the coupling precursors (C1), (C2), and (C3). Sugar (C1) is prepared by reacting lactol 10A with acetic anhydride. Sugar (C2) is prepared by treatment of sugar (C1) with hydrochloric acid. Sugar (C3) is prepared by treatment of either lactol (10A) or sugar (C1).

Scheme 6 shows one embodiment of the process for preparing the compounds of Formula (IA), wherein X, Y, Z, $Z^1$ and LG are as set forth above.

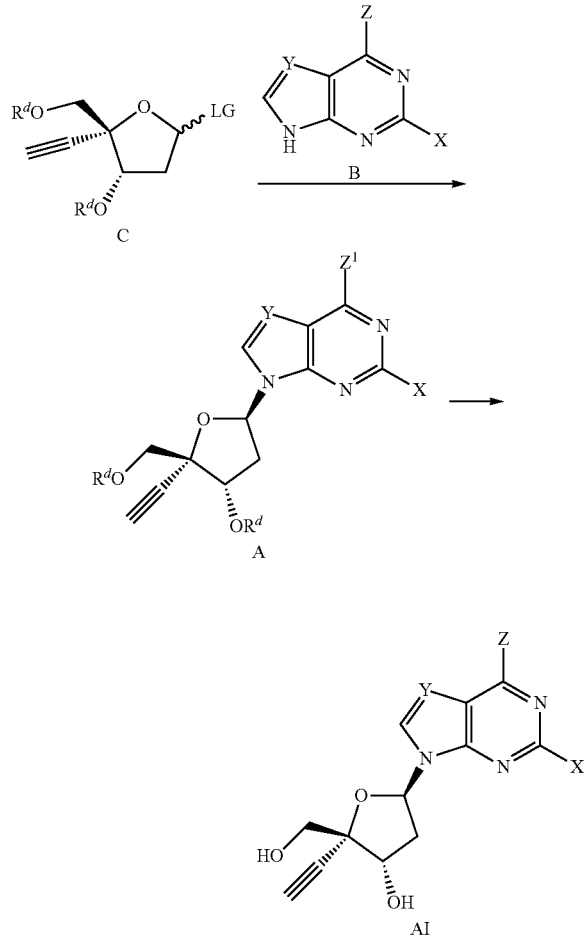

As shown in Scheme 6, sugar (C) is coupled with nucleobase (B) to provide the protected nucleoside (A). Protected nucleoside (A) is converted to the compound of Formula (IA).

Scheme 7 shows one embodiment of a process for preparing EFdA (wherein in the compound of Formula IA, X is F, Y is N, and Z is $NH_2$).

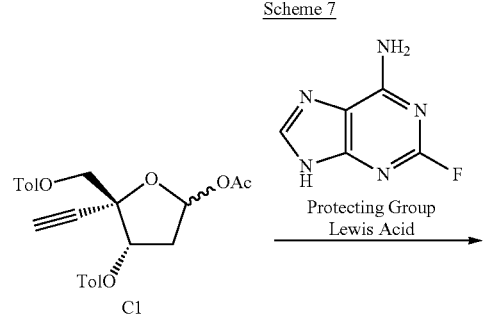

The amino group of 2-fluoroadenine is protected with a protecting group. In specific embodiments, the amino protecting group is a trimethylsilyl group. The reaction mixture containing the nucleobase is combined with the sugar (C1) to provide the protected nucleoside (A1) in the presence of a Lewis acid. Conversion of the protected nucleoside (A1) to yield EFdA can be effected by treatment with an alkali metal $C_1$-$C_3$ alkoxide which (e.g., $NaOCH_3$) cleaves both the p-toluoyl and the TMS groups. In alternative embodiments, the conversion can be affected by treatment with $NH_3$ in a $C_1$-$C_3$ alcohol, such as methanol.

In specific aspects of this embodiment, 2-fluoroadenine is treated with an excess of BTMSA and a Lewis acid such as TMS-OTf. The reaction mixture containing the nucleobase is combined with the sugar (C1) to provide the protected nucleoside (A1) wherein the amino group is protected with a TMS group, such that $Z^1$ is —$N(H)Si(CH_3)_3$. Isolation of the protected nucleoside (A1) containing the TMS-protected amino group is advantageous because the desired β-anomer selectively crystallizes from the reaction mixture after concentration of the reaction mixture and cooling. In some embodiments, the isolated protected nucleoside (A1) shows over a 99:1 ratio favoring the desired β-anomer. This feature obviates the need for column chromatography purification, and thus reduces the environmental- and cost-burdens associated with using large volumes of organic solvent for eluting the column.

Scheme 8 shows another embodiment of a process for preparing EFdA, wherein $R^s$ is as set forth above.

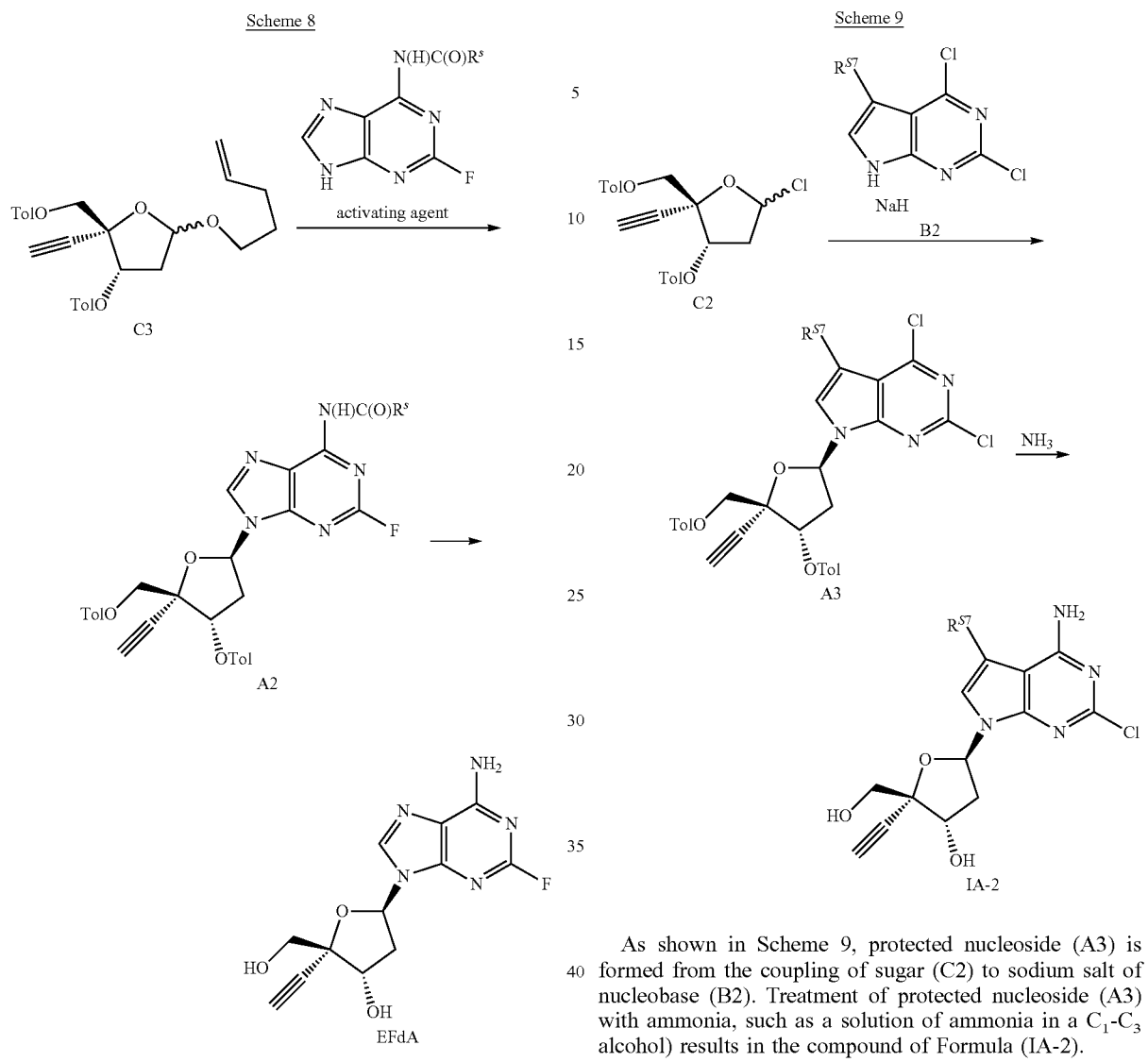

As shown in Scheme 8, sugar (C3) is activated with an activating agent, such as iodine, and then coupled with a carbamate-protected 2-fluoradenine to provide the protected nucleoside (A2). Conversion of the protected nucleoside to EFdA is effected by removal of the carbamate and p-toluoyl protecting groups.

In specific aspects of this embodiment, the amino group in the nucleobase and the protected nucleoside is protected with a Boc group. Treatment of the Boc-protected nucleoside (A2) with an alkali metal $C_1$-$C_3$ alkoxide (e.g., $NaOCH_3$) cleaves the p-toluoyl groups on the sugar moiety, and treatment with a strong acid (e.g., TFA) removes the carbamate protecting group to provide EFdA. In some embodiments, the Boc-protected nucleoside (A2) is treated with the strong acid before treatment with an alkali metal $C_1$-$C_3$ alkoxide. In other embodiments, treatment with the alkali metal $C_1$-$C_3$ alkoxide occurs before treatment with the strong acid.

Scheme 9 shows a general method suitable for preparing 4'-ethynyl-2'-deoxyribonucleosides having substituted 7-deaza adenine moieties, wherein $R^{S7}$ is H, F, Cl, or Br.

As shown in Scheme 9, protected nucleoside (A3) is formed from the coupling of sugar (C2) to sodium salt of nucleobase (B2). Treatment of protected nucleoside (A3) with ammonia, such as a solution of ammonia in a $C_1$-$C_3$ alcohol) results in the compound of Formula (IA-2).

General Chemical Procedures: All reagents were either purchased from common commercial sources or synthesized according to literature procedures beginning from commercial reagents. Commercial reagents were used without further purification. Unless otherwise indicated, percent is percent by weight given the component and the total weight of the composition, temperature is in ° C. or is at ambient temperature and pressure is at or near atmospheric. $^1$H NMR spectra were obtained on a Varian VNMR System 400 (400 MHz) and are reported as ppm downfield from $Me_4Si$ with number of protons, multiplicities, and coupling constants in Hertz indicated parenthetically. Where LC/MS data are presented, analyses were performed using an Agilent 6110A MSD or an Applied Biosystems API-100 mass spectrometer. The parent ion is given. Preparative HPLC was performed on a Waters preparative HPLC system fitted with a Waters Xselect.C18 column, typically using gradient elution with water/acetonitrile containing 0.075% trifluoro acetic acid. Flash column chromatography was performed using pre-packed normal phase silica from Biotage, Inc. or bulk silica from Fisher Scientific. Unless otherwise indicated, column chromatography was performed using a gradient elution of petroleum ether/ethyl acetate, from petroleum ether 100% to 100% ethyl acetate. The term "room temperature" in the examples refers to the ambient temperature which was typically in the range of about 20° C. to about 26° C.

Example 1

Synthesis of (2R,3S,5R)-5-(4-amino-2-chloro-5-fluoro-7H-pyrrolo[2,3-d]pyrimidin-7-yl)-2-ethynyl-2-(hydroxymethyl)tetrahydrofuran-3-ol (1)

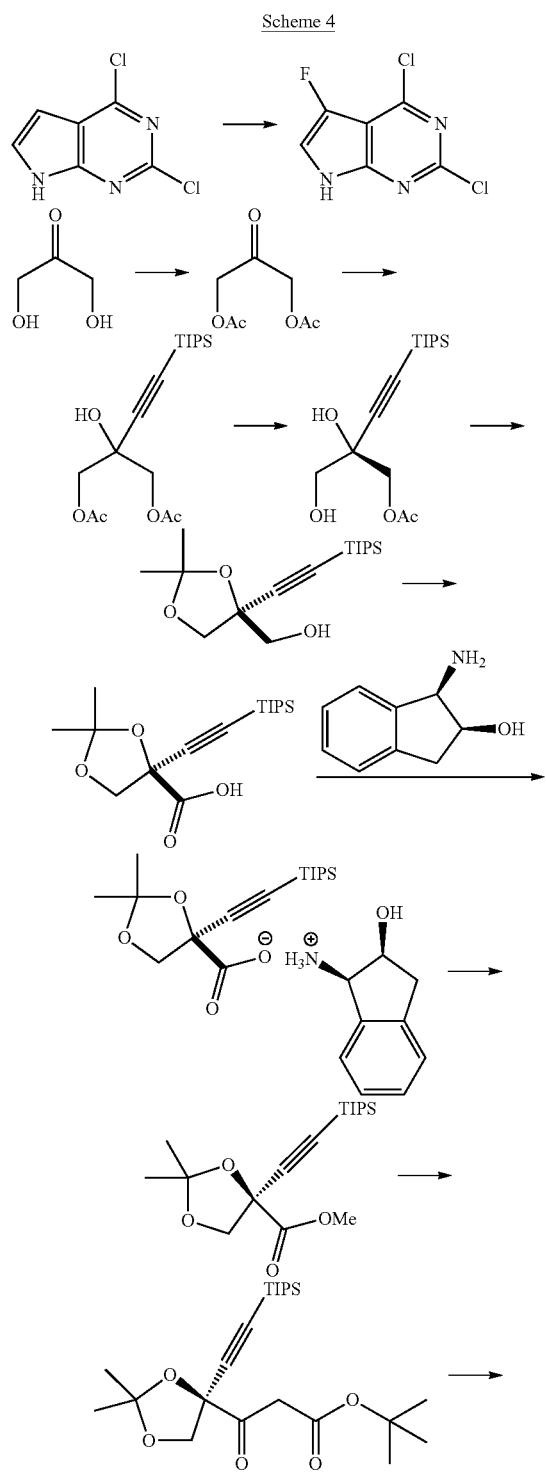

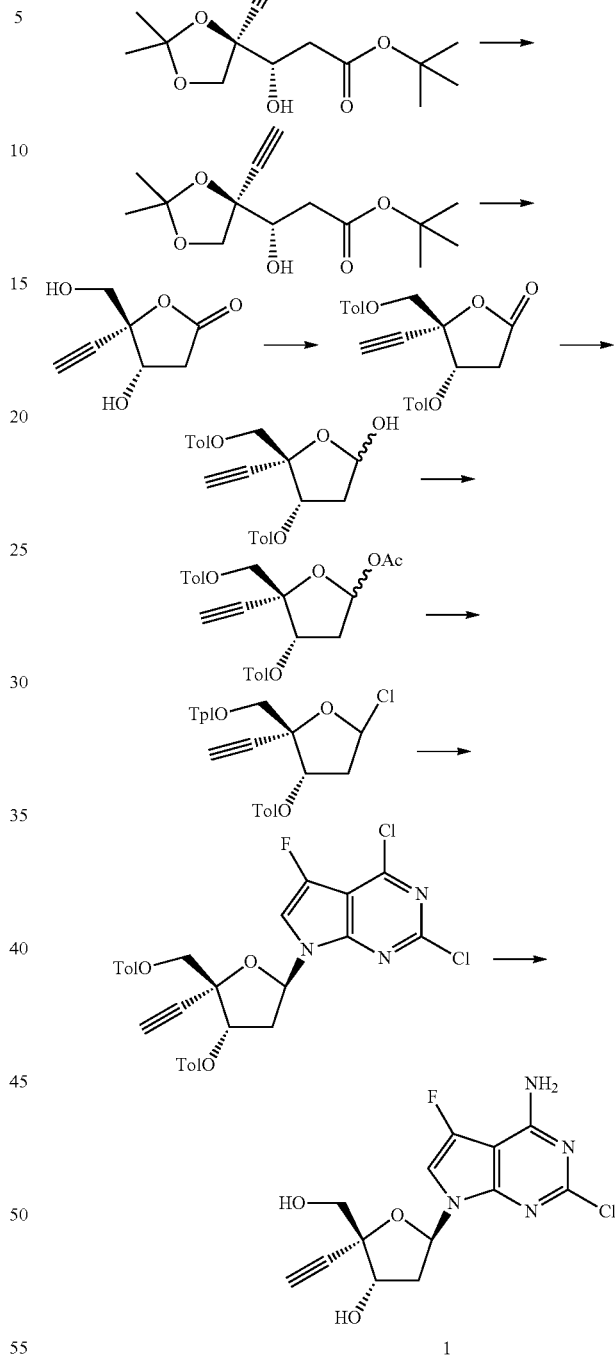

Step 1: Synthesis of 2,4-dichloro-5-fluoro-7H-pyrrolo[2,3-d]pyrimidine 2,4-dichloro-7H-pyrrolo[2,3-d]pyrimidine (1 g, 5.32 mmol) was massed into a 250 mL round-bottom flask and dried over $P_2O_5$ under vacuum overnight. To this were injected acetonitrile (60 mL) and acetic acid (12 mL) at room temperature, followed by the addition of 1-(chloromethyl)-4-fluoro-1,4-diazabicyclo[2.2.2]octane-1,4-diium tetrafluoroborate (2.64 g, 7.45 mmol) under argon atmosphere. The mixture was heated to 70° C. and stirred for 36 hours. The resulting mixture was cooled to 25° C., diluted with DCM (150 mL), washed with water (2×50 mL) and brine (2×50 mL) successively. The organic layer was collected, dried over anhydrous $Na_2SO_4$, filtered and the filtrate was concentrated under reduced pressure. silica gel column using ethyl acetate/petroleum ether (0% to 20% EtOAc in Pet. ether) to give a crude solid, which was further purified by C18 gel column reverse-phase-chromatography with the following conditions: Column, 60 A, 120 g; mobile phase, water (with 0.05% TFA) and acetonitrile (5% acetonitrile up to 40% in 15 min, 40% up to 47% in 5 min, hold 47% 5 min, up to 95% in 3 min, down to 5% in 5 min); Detector, UV 254 nm. The product-containing fractions were collected, extracted with EtOAc (2×50 mL). The organic layer was collected, washed with brine (2×30 mL), dried over anhydrous $Na_2SO_4$, filtered and the filtrate was concentrated under reduced pressure to give 2,4-dichloro-5-fluoro-7H-pyrrolo[2,3-d]pyrimidine. LC-MS: (ES, m/z): 206.05 $[M+H]^+$. $^1$H-NMR: (300 MHz, $d_6$-DMSO, ppm): δ 12.71 (brs, 1H), 7.77 (d, J=2.4 Hz, 1H). $^{19}$F-NMR: (282 MHz, $d_6$-DMSO, ppm): δ −169.79 (s, 1F).

Step 2: Synthesis of 2-oxopropane-1,3-diyl diacetate

To a solution of 1,3-dihydroxypropan-2-one (90 g, 999 mmol) in pyridine (400 ml) was added acetic anhydride (408 g, 3997 mmol) at 0° C. After the resulting mixture was stirred at 20° C. for 16 hours, it was concentrated under reduced pressure. The residue was diluted with DCM (1000 mL), washed with 2N HCl (2×1000 mL), $NaHCO_3$ (3×1000 mL). The combined organic layers was dried with anhydrous $Na_2SO_4$, filtered, and concentrated under reduced pressure. The residue was poured into stirring petroleum ether (1500 mL), the product was precipitated out and filtered to give 2-oxopropane-1,3-diyl diacetate. H-NMR: (300 MHz, $CDCl_3$, ppm): δ 4.76 (s, 4H), 2.18 (s, 6H).

Step 3: Synthesis of 2-hydroxy-2-((triisopropylsilyl)ethynyl)propane-1,3-diyl diacetate To a solution of ethynyltriisopropylsilane (58.6 g, 322 mmol) in THF (500 ml) under argon was added n-butyllithium (127 mL, 318 mmol) dropwise with stirring at −78° C. The resulting solution was stirred for 1 hour at −60° C. To this solution was added a solution of 2-oxopropane-1,3-diyl diacetate (56 g, 322 mmol) in THF (100 mL) dropwise with stirring at −78° C. The resulting solution was allowed to react, with stirring, for an additional 1 hour at −60° C. The reaction was then quenched by the addition of 25 mL of AcOH at −78° C. The resulting solution was diluted with 500 mL of MTBE. The resulting mixture was washed with 1×450 mL of citric acid (10%). The combined organic extracts were washed with 2×300 mL of brine, dried over anhydrous sodium sulfate and concentrated under vacuum to give 2-hydroxy-2-((triisopropylsilyl)ethynyl)propane-1,3-diyl diacetate as a liquid. H-NMR: (300 MHz, $CDCl_3$, ppm): δ 4.26 (d, d, J=11.4 Hz, 13.2 Hz, 4H), 3.22-3.05 (bs, 1H), 2.11 (s, 6H), 1.09-0.99 (m, 21H).

Step 4: Synthesis of (R)-2-hydroxy-2-(hydroxymethyl)-4-(triisopropylsilyl)but-3-yn-1-yl acetate To a mixture of $KH_2PO_4$/KOH (240 mL, 0.1 M, pH=7.5) and NovoCor AD L (60 g, 140 mmol) was added a solution of 2-hydroxy-2-((triisopropylsilyl)ethynyl)propane-1,3-diyl diacetate (50 g, 140 mmol) in methanol (240 ml) under argon at ambient temperature. The resulting solution was stirred for 16 hours at 30° C. The reaction progress was monitored by TLC. The resulting solution was diluted with 1000 ml of brine and MTBE (1000 mL), CELITE® 545 (50 g) was added, and stirred at 30° C. for 30 minutes. Then the mixture was filtered, and the filtrate was extracted with 3×1000 ml of MTBE. The organic layers combined washed with brine (3×500 ml), dried over anhydrous magnesium sulfate and filtered. The filtrate was concentrated under reduced pressure to afford (R)-2-hydroxy-2-(hydroxymethyl)-4-(triisopropylsilyl)but-3-yn-1-yl acetate. H-NMR: (400 MHz, $CDCl_3$, ppm): δ 4.35 (d, J=11.2 Hz, 1H), 4.23 (d, J=11.2 Hz, 1H) 3.75-3.65 (d, d, J=11.2 Hz, 26.0 Hz, 2H), 2.70-2.50 (bs, 1H), 2.13 (s, 3H), 1.09-1.00 (m, 18H), 0.92-0.89 (m, 3H).

Step 5: Synthesis of (S)-(2,2-dimethyl-4-((triisopropylsilyl)ethynyl)-1,3-dioxolan-4-yl)methanol To a solution of (R)-2-hydroxy-2-(hydroxymethyl)-4-(triisopropylsilyl)but-3-yn-1-ylacetate (70 g, 223 mmol) in MTBE (350 ml) and acetonitrile (280 ml) were added PPTS (8.39 g, 33.4 mmol) and 2,2-dimethoxypropane (70 g, 672 mmol). The resulting solution was stirred for 4 hours at 50° C. This was followed by the addition of sodium methanolate (111 ml, 111 mmol) dropwise with stirring at 0° C. The resulting solution was stirred for an additional 30 minutes at 25° C., then the pH value was adjusted to 7 by 10% citric acid. The resulting mixture was diluted with 600 ml MTBE and washed with 2×200 mL of sodium bicarbonate. The combined organic layers were washed with brine (3×300 ml), dried over anhydrous sodium sulfate and concentrated under vacuum to give (S)-(2,2-dimethyl-4-((triisopropylsilyl)ethynyl)-1,3-dioxolan-4-yl)methanol. H-NMR: (300 MHz, $CDCl_3$, ppm): δ 5.30 (s 1H), 4.14-4.13 (m, 2H), 3.75-3.70 (m, 1H), 3.65-3.55 (m, 1H), 1.85-1.95 (m, 1H), 1.54 (s, 3H), 1.44 (s, 3H), 1.08-1.01 (m, 21H).

Step 6: Synthesis of (R)-2,2-dimethyl-4-((triisopropylsilyl)ethynyl)-1,3-dioxolane-4-carboxylic acid To a mixture of (S)-(2,2-dimethyl-4-((triisopropylsilyl)ethynyl)-1,3-dioxolan-4-yl)methanol (52 g, 166 mmol) in MTBE (200 ml) and acetone (165 ml) under argon were added TEMPO (2.86 g, 18.30 mmol), NaOCl (36.1 g, 399 mmol) and $NaClO_2$ (124 g, 166 mmol) in water, $NaH_2PO_4 \cdot H_2O$ (120 g) in water (600 ml) at ambient temperature. The resulting mixture was warmed to 35° C. and stirred for 4 hours under argon. The reaction progress was monitored by TLC. The reaction mixture was cooled down to ambient temperature. The organic layer was washed with 200 ml of $NaHSO_3$ and 2×200 ml of water, dried over anhydrous sodium sulfate. The filtrate was concentrated under reduced pressure to give (R)-2,2-dimethyl-4-((triisopropylsilyl)ethynyl)-1,3-dioxolane-4-carboxylic acid. H-NMR: (300 MHz, $d_6$-DMSO, ppm): δ 13.50 (s, 1H), 4.34 (d, J=8.7 Hz, 1H), 4.09 (d, J=8.7 Hz, 1H), 3.08 (s, 1H), 1.41 (s, 3H), 1.36 (s, 3H), 1.03-0.96 (m, 21H).

Step 7: Synthesis of (1R,2S)-2-hydroxy-2,3-dihydro-1H-inden-1-aminium(R)-2,2-dimethyl-4-((triisopropylsilyl)ethynyl)-1,3-dioxolane-4-carboxylate To a mixture of (R)-2,2-dimethyl-4-((triisopropylsilyl)ethynyl)-1,3-dioxolane-4-carboxylic acid (120 g, 368 mmol)) in MTBE (1000 ml) under argon was added (1R, 2S)-1-amino-2,3-dihydro-1H-inden-2-ol (49.3 g, 331 mmol) at ambient temperature. The resulting mixture was warmed to 50° C. and stirred for 4 hours under argon. After 4 hours, the solution was slowly cooled to 25° C. and stirred for 24 hours under argon. The solids were collected by filtration and washed with MTBE (3×300 ml) to give (1R,2S)-2-hydroxy-2,3-dihydro-1H-inden-1-aminium(R)-2,2-dimethyl-4-((triisopropylsilyl)ethynyl)-1,3-dioxolane-4-carboxylate. H-NMR: (300 MHz, $d_6$-DMSO, ppm): δ 7.66-7364 (m, 1H), 7.26-7.17 (m, 3H), 4.73-4.72 (m, 1H), 4.51-4.49 (m, 1H), 4.26-4.18 (m, 2H), 3.16-3.12 (m, 2H), 1.50 (s, 3H), 1.3 7 (m, 3H), 1.30-1.22 (m, 2H), 0.97 (s, 18H), 0.88-0.86 (m, 1H).

Step 8: Synthesis of (R)-methyl 2,2-dimethyl-4-((triisopropylsilyl)ethynyl)-1,3-dioxolane-4-carboxylate To a mixture of (1R,2S)-2-hydroxy-2,3-dihydro-1H-inden-1-aminium (R)-2,2-dimethyl-4-((triisopropylsilyl)ethynyl)-1,3-dioxolane-4-carboxylate (160 g, 336 mmol) in MTBE (2000 ml) was added 1000 ml of citric acid (10%) at 0° C. The mixture was stirred for 10 minutes. The organic layer was collected, washed with 3×1000 ml of brine, dried over anhydrous sodium sulfate and filtered. The filtrate was concentrated under reduced pressure to give 100 g of (4R)-2,2-dimethyl-4-[2-[tris(propan-2-yl)silyl]ethynyl]-1,3-dioxolane-4-carboxylic acid as a liquid. To 100 g of (4R)-2,2-dimethyl-4-[2-[tris(propan-2-yl)silyl]ethynyl]-1,3-dioxolane-4-carboxylic acid in DMF (1000 ml) under argon were added $Cs_2CO_3$ (329 g, 1009 mmol) and MeI (52.6 ml, 841 mmol) at ambient temperature. The resulting solution was stirred overnight at ambient temperature. The solids were filtered out. The resulting filtrate was diluted with 2500 ml of EA. The resulting mixture was washed with 3×1000 ml of brine. The combined organic layers was dried over anhydrous sodium sulfate and filtered. The filtrate was concentrated under reduced pressure to give (R)-methyl 2,2-dimethyl-4-((triisopropylsilyl)ethynyl)-1,3-dioxolane-4-carboxylate. H-NMR: (400 MHz, $CDCl_3$, ppm): δ 4.48 (d, J=8.8 Hz, 1H), 4.22 (d, J=8.8 Hz, 1H), 3.83 (s, 3H), 1.53 (s, 3H), 1.49 (s, 3H), 1.10-1.02 (m, 21H).

Step 9: Synthesis of (R)-tert-butyl 3-(2,2-dimethyl-4-((triisopropylsilyl)ethynyl)-1,3-dioxolan-4-yl)-3-oxopropanoate To a solution diisopropyl amine (53.7 g 532 mmol) in THF (500 ml) was added n-BuLi (212 ml of 2.5 mol in hexane) over 40 minutes with internal temperature maintained below −68° C. To the LDA solution was added tert-butyl acetate (61.4 g, 529 mmol) in THF (1000 ml) under argon at −78° C. The resulting mixture was stirred for 1 hour under argon (−60° C.). To the mixture was added a solution of (R)-methyl 2,2-dimethyl-4-((triisopropylsilyl)ethynyl)-1,3-dioxolane-4-carboxylate (90 g, 264 mmol) in THF (200 ml) at −78° C. The reaction progress was monitored by TLC. The resulting solution was allowed to react, with stirring, for an additional 1 hour at −78° C. The reaction was then quenched by the addition of 15 ml AcOH. The resulting solution was diluted with 2500 mL of MTBE The combined organic layers were washed with brine (4×1000 mL), dried over anhydrous sodium sulfate and filtered. The filtrate was concentrated under reduced pressure to give (R)-tert-butyl 3-(2,2-dimethyl-4-((triisopropylsilyl)ethynyl)-1,3-dioxolan-4-yl)-3-oxopropanoate. H-NMR: (300 MHz, $CDCl_3$, ppm): δ 4.52 (d, J=8.7 Hz, 1H), 4.43 (d, J=8.7 Hz, 1H), 3.68 (dd, J=16.5 Hz, 36.6 Hz, 2H), 1.49-1.45 (m, 15H), 1.09-0.98 (m, 21H).

Step 10: Synthesis of (S)-tert-butyl 3-((R)-2,2-dimethyl-4-((triisopropylsilyl)ethynyl)-1,3-dioxolan-4-yl)-3-hydroxypropanoate Under argon, to a stirred and cooled 0° C. solution of $Et_3N$ (32.8 ml, 235 mmol) in THF (50 ml) was added formic acid (27.1 g, 589 mmol). The mixture was stirred at ambient temperature for 10 minutes (flask 1). A second flask with a stirred solution of (R)-tert-butyl 3-(2,2-dimethyl-4-((triisopropylsilyl)ethynyl)-1,3-dioxolan-4-yl)-3-oxopropanoate (100 g, 235 mmol) in THF (1000 ml) and MTBE (250 ml) was added (((S,S)-TS-DENEB (0.345 g, 0.530 mmol). The prepared formic acid/$Et_3N$ mixture was added from flask 1 to flask 2. The reaction mixture was stirred at 38° C. under Ar. The reaction was monitored by TLC. After 11 hours, the reaction mixture was cooled to 22° C., then charged with 10% citric acid solution (500 mL). The mixture was stirred and the layers were split. The organic solution was treated with Ecosorb C-941(25 g). The slurry was stirred for 1 hour and filtered. The filtrate was concentrated under reduced pressure to give (S)-tert-butyl 3-((R)-2,2-dimethyl-4-((triisopropylsilyl)ethynyl)-1,3-dioxolan-4-yl)-3-hydroxypropanoate. The product was used in the next step directly without further purification. H-NMR: (400 MHz, $CDCl_3$, ppm): δ 4.22 (d, J=8.4 Hz, 1H), 4.11 (d, J=8.4 Hz, 1H), 4.03-4.02 (m, 1H), 2.78-2.70 (m, 2H), 2.48-2.39 (m, 1H), 1.50-1.41 (m, 15H), 1.08-1.04 (m, 21H).

Step 11: Synthesis of (S)-tert-butyl 3-((R)-4-ethynyl-2,2-dimethyl-1,3-dioxolan-4-yl)-3-hydroxypropanoate To a mixture of (S)-tert-butyl 3-((R)-2,2-dimethyl-4-((triisopropylsilyl)ethynyl)-1,3-dioxolan-4-yl)-3-hydroxypropanoate (40 g, 94 mmol) in THF (300 ml) under argon was added 1 M TBAF in THF (94 ml) dropwise with stirring at 0° C. After the reaction mixture was stirred for 20 minutes at 25° C., it was quenched by saturated brine (100 mL) at 0° C. The resulting mixture was diluted with MTBE (2500 mL). The organic layers were washed with brine (4×1000 mL), dried over anhydrous sodium sulfate and filtered. The filtrate was concentrated under reduced pressure to give (S)-tert-butyl 3-((R)-4-ethynyl-2,2-dimethyl-1,3-dioxolan-4-yl)-3-hydroxypropanoate. H-NMR: (400 MHz, $CDCl_3$, ppm): δ 4.21 (d, d, J=8.4 Hz, 40.0 Hz, 2H), 4.17-4.15 (m, 1H), 3.30-3.20 (brs, 1H), 2.72-2.71 (m, 1H), 2.56-2.54 (m, 2H), 1.50-1.47 (m, 15H).

Step 12: Synthesis of (4S,5R)-5-ethynyl-4-hydroxy-5-(hydroxymethyl)dihydrofuran-2(3H)-one To a mixture of (S)-tert-butyl 3-((R)-4-ethynyl-2,2-dimethyl-1,3-dioxolan-4-yl)-3-hydroxypropanoate (40 g, 148 mmol) in 1,2-DME (200 ml) was added HCl (36.5 ml, 444 mmol) dropwised with stirring at 0° C. over 2 minutes. After the mixture was stirred at 45° C. for 1 hour, it was concentrated under reduced pressure. Isopropyl acetate (50 ml) was added to the residue dropwise with stirring at ambient temperature for 16 h. The solid was collected by filtration to give (4S,5R)-5-ethynyl-4-hydroxy-5-(hydroxymethyl)dihydrofuran-2(3H)-one. H-NMR: (400 MHz, DMSO, ppm): δ

5.82 (d, J=5.6 Hz, 1H), 5.56 (t, J=6.0 Hz, 12.0 Hz, 1H), 4.75 (s, 1H), 4.38-4.34 (m, 2H), 2.94-2.87 (m, 1H), 2.39-2.34 (m, 1H).

Step 13: Synthesis of (2R,3S)-2-ethynyl-2-(((4-methylbenzoyl)oxy)methyl)-5-oxotetrahydrofuran-3-yl 4-methylbenzoate To a mixture of (4S,5R)-5-ethynyl-4-hydroxy-5-(hydroxymethyl)dihydrofuran-2(3H)-one (8.5 g, 54.4 mmol) in pyridine (90 mL) under argon was added 4-methylbenzoyl chloride (15.11 mL, 114 mmol) at 0° C. The resulting mixture was stirred for 2 hours at 0° C. under an atmosphere of argon. The reaction mixture was poured into ice water (300 mL) and stirred for 10 minutes. The mixture was filtered, the filter cake was washed with ice water (10×100 mL), and then dried at 25° C. for 24 hours to afford (2R,3S)-2-ethynyl-2-(((4-methylbenzoyl)oxy)methyl)-5-oxotetrahydrofuran-3-yl 4-methylbenzoate. LC-MS: (ES, m/z): 393.20 [M+H]$^{-1}$, H-NMR (300 MHz, CDCl$_3$, ppm): δ 8.00 (d, J=8.1 Hz, 2H), 7.91 (d, J=8.1 Hz, 2H), 7.30-7.25 (m, 4H), 5.85-5.82 (m, 1H), 4.77 (dd, J=9.0 Hz, 2H), 3.27-3.18 (m, 1H), 2.94-2.87 (m, 1H), 2.73 (s, 1H), 2.44 (d, J=3.9 Hz, 6H).

Step 14: Synthesis of (2R,3S)-2-ethynyl-5-hydroxy-2-(((4-methylbenzoyl)oxy)methyl)tetrahydrofuran-3-yl 4-methylbenzoate To a stirred solution of methyl (2R,3S)-2-ethynyl-2-(((4-methylbenzoyl)oxy)methyl)-5-oxotetrahydrofuran-3-yl 4-methylbenzoate (1160 mg, 2.96 mmol) in anhydrous toluene (30 mL) and DCM (6 mL) under argon in a 100-mL 3-necked round-bottom flask, was added bis(2-methoxyethoxy)aluminum(III) sodium hydride toluene solution (70% w/w, 0.598 g, 2.96 mmol) dropwise with stirring at −78° C. in 3 minutes. The resulting solution was stirred at the same temperature for 90 minutes. The reaction progress was monitored by TLC. The reaction was quenched by the addition of acetic acid (1.7 mL), then hydrochloric acid (1 N, 30 mL) was added and the mixture was extracted with ethyl acetate (3×30 mL). The combined organic fractions were washed with brine (saturated, 2×30 mL), dried over anhydrous sodium sulfate, filtered and concentrated under vacuum. The residue was purified by silica gel column chromatography with ethyl acetate/petrol ether (15/85) to give (2R,3S)-2-ethynyl-5-hydroxy-2-(((4-methylbenzoyl)oxy)methyl)tetrahydrofuran-3-yl 4-methylbenzoate. H-NMR: (300 MHz, CDCl$_3$, ppm): δ 7.92-8.00 (m, 4H), 7.19-7.27 (m, 4H), 5.74-5.84 (m, 1H), 5.65-5.70 (m, 1H), 4.68 (s, 1H), 4.54 (dd, J=11.4 Hz, 35.4 Hz, 1H), 2.49-2.61 (m, 2.5H), 2.36-2.42 (m, 6.5H).

An alternative preparation is described below which omits the chromatographic purification.

To a stirred solution of methyl (2R,3S)-2-ethynyl-2-(((4-methylbenzoyl)oxy)methyl)-5-oxotetrahydrofuran-3-yl 4-methylbenzoate (4.5 g, 22.94 mmol) in toluene (67.5 mL) and DCM (9 mL) was added bis(2-methoxyethoxy)aluminum(III) sodium hydride toluene solution (65% w/w, 0.3.57 g, 11.47 mmol) dropwise with stirring at −60° C. over 2 hours. The resulting solution was stirred at the same temperature for 2 hours. The reaction progress was monitored by LC. The reaction was quenched by the addition of acetic acid (1.31 mL, 22.94 mmol) over 20 minutes, keeping the temperature below −60° C. MTBE (22.50 mL) was added, followed by aqueous citric acid solution (10 wt %, 22.5 mL) and hydrochloric acid (1 N; 90.0 mL). The organic phase was separated, dried over anhydrous magnesium sulfate, filtered and concentrated under vacuum to give (2R,3S)-2-ethynyl-5-hydroxy-2-(((4-methylbenzoyl)oxy)methyl)tetrahydrofuran-3-yl 4-methylbenzoate. The product was used in the next transformation without further purification.

Step 15: Synthesis of (2R,3S)-5-acetoxy-2-ethynyl-2-(((4-methylbenzoyl)oxy)methyl)tetrahydrofuran-3-yl 4-methylbenzoate To a stirred solution of methyl (2R,3S)-2-ethynyl-5-hydroxy-2-(((4-methylbenzoyl)oxy)methyl)tetrahydrofuran-3-yl 4-methylbenzoate (925 mg, 2.345 mmol) in dried DCM (30 mL) under argon in a 100-mL 3-necked round-bottom flask, was added 4-dimethylaminopyridine (430 mg, 3.52 mmol), followed by the addition of a solution of acetic anhydride (0.332 ml, 3.52 mmol) in dichloromethane (3 mL) dropwise with stirring at 0° C. The resulting solution was stirred at 0° C. for 1 hour. The reaction was quenched with water (30 mL) and extracted with dichloromethane (3×30 mL). The combined organic layer was washed with brine (2×30 mL), dried over anhydrous sodium sulfate, filtered and concentrated under vacuum. The residue was purified by silica gel column chromatography with ethyl acetate/petrol ether (10/90) to give (2R,3S)-5-acetoxy-2-ethynyl-2-(((4-methylbenzoyl)oxy)methyl)tetrahydrofuran-3-yl 4-methylbenzoate. H-NMR: (300 MHz, CDCl$_3$, ppm): δ 7.90-8.10 (m, 4H), 7.19-7.27 (m, 4H), 6.45-6.50 (m, 1H), 5.84 (t, J=7.5 Hz, 1H), 4.72-4.75 (d, J=11.7 Hz, 1H), 4.50-4.61 (m, 1H), 2.64-2.78 (m, 3H), 2.40-2.43 (m, 6H), 1.90 (s, 3H).

An alternative preparation is described below which omits the chromatographic purification.

To a stirred suspension of methyl (2R,3S)-2-ethynyl-5-hydroxy-2-(((4-methylbenzoyl)oxy)methyl)tetrahydrofuran-3-yl 4-methylbenzoate (26.0 g, 65.9 mmol) in DCM (130 mL) at 0° C. was added acetic anhydride (9.35 mL, 99 mmol), triethylamine (11.91 mL, 86 mmol), and 4-dimethylaminopyridine (1.61 g, 13.18 mmol). The resulting solution was stirred at 0° C. for 2.5 hours then quenched with MTBE (650 mL) and aqueous citric acid (10 wt %; 130 mL). The organic layer was washed with aqueous citric acid (10 wt %; 130 mL) and water (3×130 mL), then concentrated under vacuum to give (2R,3S)-5-acetoxy-2-ethynyl-2-(((4-methylbenzoyl)oxy)methyl)tetrahydrofuran-3-yl 4-methylbenzoate. The product was used in the next transformation without further purification.

Step 16: Synthesis of (2R,3S)-5-chloro-2-ethynyl-2-(((4-methylbenzoyl)oxy)methyl)tetrahydrofuran-3-yl 4-methylbenzoate Methyl (2R,3S)-5-acetoxy-2-ethynyl-2-(((4-methylbenzoyl)oxy)methyl)tetrahydrofuran-3-yl 4-methylbenzoate (7 g, 16.04 mmol) was dried over P$_2$O$_5$ under vacuum overnight and then added into an oven dried 250 ml round-bottom flask, followed by the addition of dry DCM (140 mL) under argon atmosphere at room temperature. The mixture was stirred until it became clear, then cooled to 0° C. HCl gas was bubbled into the mixture while maintaining the temperature below 5° C. The reaction progress was monitored by LCMS. After bubbling was continued for 30 minutes then argon was bubbled into the mixture for 10 minutes to remove the dissolved residual HCl. The resulting DCM solution was partitioned between cold biphasic mixture of MTBE (210 mL) and aqueous NaHCO$_3$ (saturated, 105 mL). The organic layer was collected, washed with cold aqueous NaHCO$_3$ (saturated, 2×105 mL), dried over anhydrous MgSO₄ and filtered. The filtrate was concentrated under reduced pressure to give (2R,3S)-5-chloro-2-ethynyl-2-(((4-methylbenzoyl)oxy)methyl)tetrahydrofuran-3-yl 4-methylbenzoate (α/β=2/1), which was used to next reaction step directly without further purification. LC-MS: (ES, m/z): 1) Cl converted to OH, 417.25 [M+Na]⁺, 377.36 [M−OH]⁺. 2) Cl converted to OMe, 431.34 [M+Na]⁺, 377.36 [M−OMe]⁺. H-NMR: (400 MHz, CD₃CN, ppm): δ 8.02 (d, J=8.0 Hz, 41H), 7.96-7.93 (m, 3H), 7.36-7.26 (m, 4H), 6.50-6.48 (m, 1H), 5.94 (t, J=8.0 Hz, 0.3H), 5.79 (dd, J=1.2 Hz, J=7.2 Hz, 0.6H), 4.78 (d, J=11.6 Hz, 0.32H), 4.57 (d, J=12.0 Hz, 0.32H), 4.50 (dd, J=11.2 Hz, J=14.4 Hz, 1.21H), 4.51-4.47 (m, 1H), 3.06-3.04 (m, 1H), 2.98-2.91 (m, 1.4H), 2.74 (d, J=15.6 Hz, 0.6H), 2.42-2.39 (m, 6H).

Step 17: Synthesis of (2R,3S,5R)-5-(2,4-dichloro-5-fluoro-7H-pyrrolo[2,3-d]pyrimidin-7-yl)-2-ethynyl-2-(((4-methylbenzoyl)oxy)methyl)tetrahydrofuran-3-yl 4-methylbenzoate To a stirred solution of 2,4-dichloro-5-fluoro-7H-pyrrolo[2,3-d]pyrimidine (550 mg, 2.67 mmol) in anhydrous THF (18 mL) under argon atmosphere was injected 1M NaHMDS in THF (2.67 mL, 2.67 mmol) at −20° C. in 5 minutes. The resulting mixture was maintained at −20° C. for 30 minutes and then gradually warmed to 20° C. To the above was injected a solution of (2R,3S)-5-chloro-2-ethynyl-2-(((4-methylbenzoyl)oxy)methyl)tetrahydrofuran-3-yl 4-methylbenzoate (918 mg, 2.223 mmol) in anhydrous THF (18 mL) in 5 minutes. The resulting mixture was stirred at 20° C. for 6 hours. The reaction was quenched by the addition of diluted aqueous HCl (0.5 N, 5 mL) and extracted with MTBE (3×50 mL). The organic layer was collected, washed with brine (2×30 mL), dried over anhydrous MgSO₄ and filtered. The filtrate was concentrated under reduced pressure, the residue was purified by silica gel column using ethyl acetate/petroleum ether (0% to 10% EtOAc in pet. ether) to give a crude product. The crude product (α+β mixture) was treated with MTBE (4 mL) stirred at room temperature for 15 hours. A solid was precipitated from the medium and was collected by filtration, washed with cold MTBE (2 mL), and dried under vacuum to give (2R,3S,5R)-5-(2,4-dichloro-5-fluoro-7H-pyrrolo[2,3-d]pyrimidin-7-yl)-2-ethynyl-2-(((4-methylbenzoyl)oxy)methyl)tetrahydrofuran-3-yl 4-methylbenzoate. ¹H-NMR- (β isomer): (300 MHz, CDCl₃, ppm): δ 8.02 (d, J=8.1 Hz, 2H), 7.90 (d, J=8.1 Hz, 2H), 7.29 (d, J=8.1 Hz, 2H), 7.25 (d, J=8.1 Hz, 2H), 7.09 (d, J=2.7 Hz, 1H), 6.83 (t, J=6.0 Hz, 1H), 5.90 (t, J=6.3 Hz, 1H), 4.83 (d, J=12.0 Hz, 1H), 4.61 (d, J=12.0 Hz, 1H), 2.87 (t, J=6.3 Hz, 2H), 2.71 (s, 1H), 2.45, 2.43 (2s, 6H). ¹⁹F-NMR (β isomer): (282 MHz, CDCl₃, ppm): β−165.25 (s, 1F). LC-MS: (ES, m/z): 582.40 [M+H]⁺.

Step 18: Synthesis of (2R,3S,5R)-5-(4-amino-2-chloro-5-fluoro-7H-pyrrolo[2,3-d]pyrimidin-7-yl)-2-ethynyl-2-(hydroxymethyl)tetrahydrofuran-3-ol (1)

(2R,3S,5R)-5-(2,4-dichloro-5-fluoro-7H-pyrrolo[2,3-d]pyrimidin-7-yl)-2-ethynyl-2-(((4-methylbenzoyl)oxy)methyl)tetrahydrofuran-3-yl 4-methylbenzoate (240 mg, 0.412 mmol) was massed into an oven-dried 80 ml steel bomb and cooled to −40° C. To the above was added isopropanolic ammonia (i-PrOH/liquid NH₃=1/1, v/v, mixed at −40° C., 30 mL). After the resulting mixture was heated to 80° C. and stirred for 16 hours, it was cooled to room temperature and then concentrated under reduced pressure. The residue was purified by silica gel column chromatography using DCM/MeOH (94/6) to give a crude solid. The crude was triturated with DCM/MeOH (20/1, v/v, 4 mL) and stirred at room temperature for 2 hours. A precipitate was formed and then collected by filtration, washed with DCM/MeOH (v/v, 20/1, 2×2 mL) and lyophilized overnight to give (2R,3S,5R)-5-(4-amino-2-chloro-5-fluoro-7H-pyrrolo[2,3-d]pyrimidin-7-yl)-2-ethynyl-2-(hydroxymethyl)tetrahydrofuran-3-ol. ¹H-NMR: (300 MHz, d₆-DMSO, ppm): δ 7.68 (brs, 2H), 7.32 (d, J=2.0 Hz, 1H), 6.44 (t, J=5.8 Hz, 1H), 5.52 (d, J=5.6 Hz, 1H), 5.27 (t, J=6.0 Hz, 1H), 4.44 (q, J=6.4 Hz, 1H), 3.60 (q, J=6.0 Hz, 1H), 3.53 (q, J=6.4 Hz, 1H), 3.48 (s, 1H), 2.48-2.41 (m, 1H), 2.37-2.30 (m, 1H). ¹⁹F-NMR: (282 MHz, d₆-DMSO, ppm): δ −166.67 (s, 1F). LC-MS: (ES, m/z): 327.00 [M+H]⁺.

Example 2

Synthesis of ammonium ((2R,3S,5R)-5-(4-amino-2-chloro-5-fluoro-7H-pyrrolo[2,3-d]pyrimidin-7-yl)-2-ethynyl-3-hydroxytetrahydrofuran-2-yl)methyl triphosphate (2)

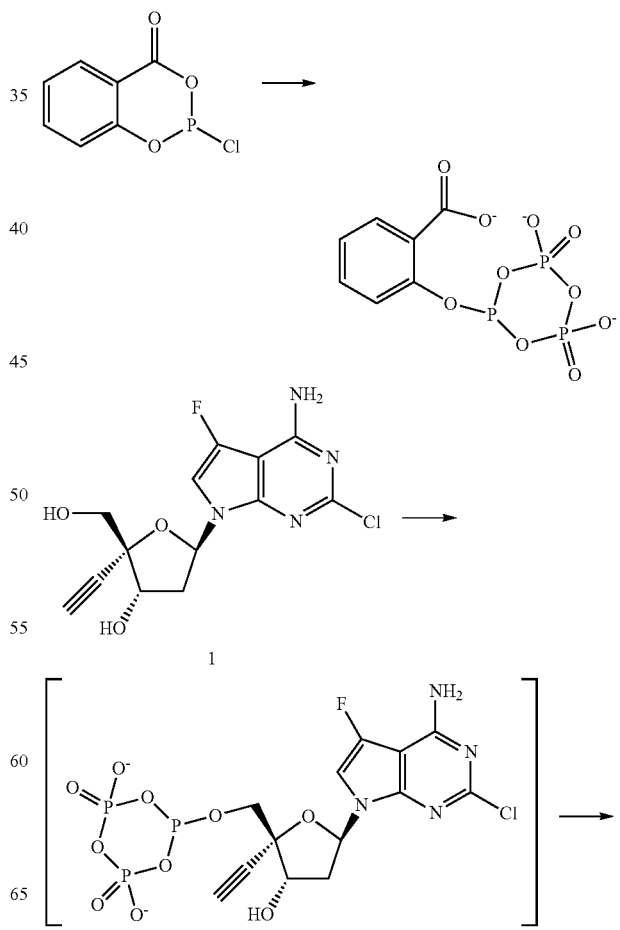

-continued

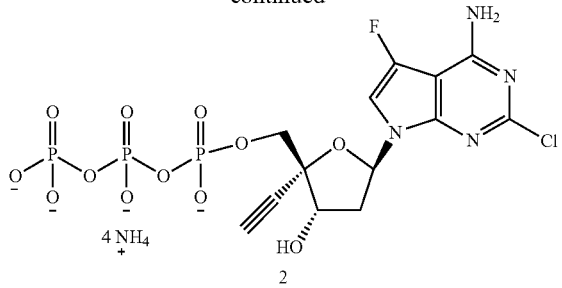

2

Step 1: Synthesis of 2-((4,4,6,6-tetraoxido-1,3,5,2,4,6-trioxatriphosphinan-2-yl)oxy)benzoate In a glove box under an argon atmosphere, dry tributylamine (0.4 ml, 1.679 mmol) was added to the flask containing tributylammonium pyrophosphate (112 mg, 0.205 mmol) dissolved in 0.4 mL dimethylformamide (DMF) to give a clear solution. The clear solution was then injected into the flask containing dry 2-chloro-4H-benzo[d][1,3,2]dioxaphosphinin-4-one (27.6 mg, 0.136 mmol) in dimethylformamide (0.4 mL) under vigorous stirring. The resulting mixture was stirred at 30° C. for 30 min to give 2-((4,4,6,6-tetraoxido-1,3,5,2,4,6-trioxatriphosphinan-2-yl)oxy)benzoate which was used to the next reaction directly without any work-up.

Step 2: Synthesis of ammonium ((2R,3S,5R)-5-(4-amino-2-chloro-5-fluoro-7H-pyrrolo[2,3-d]pyrimidin-7-yl)-2-ethynyl-3-hydroxytetrahydrofuran-2-yl)methyl triphosphate (2)

(2R,3S,5R)-5-(4-amino-2-chloro-5-fluoro-7H-pyrrolo[2,3-d]pyrimidin-7-yl)-2-ethynyl-2-(hydroxymethyl)tetrahydrofuran-3-ol (20 mg, 0.061 mmol) was massed into a 10 mL over-dried round-bottom flask and then dried over $P_2O_5$ under high vacuum overnight. To this flask was added activated molecular sieves 4 Å (300 mg). Under argon atmosphere, a solution of 2-((4,4,6,6-tetraoxido-1,3,5,2,4,6-trioxatriphosphinan-2-yl)oxy)benzoate (1.8 eq, freshly prepared) in dry DMF (0.6 ml) was transferred into the above flask by syringes and the mixture was stirred at 30° C. for 3 h. The reaction progress was monitored by TLC (acetonitrile:0.1 M ammonium chloride=7:3). When most of started nucleoside was consumed, the mixture was cooled to 0° C., followed by the injection of iodine solution [3% iodine in pyridine/water (9/1), ~0.5 mL]. As the iodine was consumed, drop-wise addition of the iodine solution was continued until a permanent brown color of iodine was maintained. After 15 min, triethylammonium bicarbonate buffer (1.0 M, 1.0 mL) was added with stirring at 10° C. and the mixture was stirred for 15 min. The volatile was removed under reduced pressure (inner temperature was not over 25° C.). The residue was re-dissolved in water (2 mL) and extracted with chloroform (2×2 mL). The collected aqueous layer which containing crude product was then purified by preparative-HPLC with the following conditions (1 #-Pre-HPLC-011(Waters)): Column: X Bridge Prep Amide, 19*150 mm, 5 um; Mobile phase: water with 50 mmol ammonium bicarbonate and acetonitrile (90% acetonitrile to 55% in 10 min, up to 30% in 2 min); Detector, UV 254 & 220 nm. The product-containing fractions were collected and concentrated to an approximate volume of 10 mL. Then ACN (1 mL) and TEAB buffer (2 M, 0.05 mL) were added to the solution, and then the mixture was lyophilized for 40 h to give ammonium ((2R,3S,5R)-5-(4-amino-2-chloro-5-fluoro-7H-pyrrolo[2,3-d]pyrimidin-7-yl)-2-ethynyl-3-hydroxytetrahydrofuran-2-yl)methyl triphosphate. LC-MS: (ES, m/z): 564.95 [M−H−4NH$_3$]$^−$. H-NMR: (400 MHz, D$_2$O, ppm): δ 7.07 (s, 1H), 6.46 (s, 1H), 4.15-4.05 (m, 2H), 2.56-2.49 (m, 2H). P-NMR: (161 MHz, D$_2$O, ppm): δ −5.81 (s, 1P), −11.49−−11.41 (d, J=13.20 Hz, 1P), −19.28 (s, 1P).

Example 3

Synthesis of (2R,3S,5R)-5-(6-amino-2-fluoro-9H-purin-9-yl)-2-ethynyl-2-(hydroxymethyl)tetrahydrofuran-3-ol (EFdA) from (2R,3S)-5-acetoxy-2-ethynyl-2-(((4-methylbenzoyl)oxy)methyl)tetrahydrofuran-3-yl 4-methylbenzoate

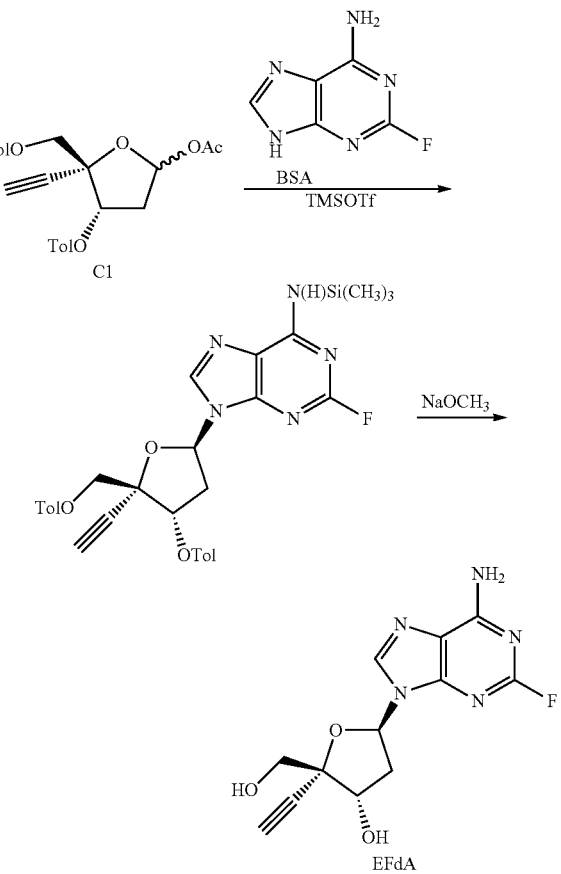

Step 1: Synthesis of (2R,3S,5R)-2-ethynyl-5-(2-fluoro-6-((trimethylsilyl)amino)-9H-purin-9-yl)-2-(((4-methylbenzoyl)oxy)methyl)tetrahydrofuran-3-yl 4-methylbenzoate To a stirred solution of 2-fluoro-7H-purin-6-amine (4.79 g, 31.3 mmol) in MeCN (210 mL) was added N,O-bis(trimethylsilyl)acetamide (35.3 mL, 144 mmol). The reaction mixture was heated to 81° C. and stirred for 1 hour. The resulting solution was cooled to room temperature and trimethylsilyl trifluoromethanesulfonate (7.84 mL, 43.3 mmol) was added, followed by acetonitrile (105 mL). To the above was added a solution of (2R,3S)-5-acetoxy-2-ethynyl- 2-(((4-methylbenzoyl)oxy)methyl)tetrahydrofuran-3-yl 4-methylbenzoate (10.5 g, 24.06 mmol) in MeCN (100 mL) over 2 hours. The resulting mixture was stirred at 81° C. for 14 hours, then concentrated to 150 mL volume by simple distillation. The reaction mixture was seeded with product (0.1 wt %) and slowly cooled to room temperature to give a slurry. The solid was collected by filtration to give (2R,3S,5R)-2-ethynyl-5-(2-fluoro-6-((trimethylsilyl)amino)-9H-purin-9-yl)-2-(((4-methylbenzoyl)oxy)methyl)tetrahydrofuran-3-yl 4-methylbenzoate (6.73 g). $^{1}$H-NMR-(β isomer): (400 MHz, CDCl$_3$, ppm): δ 8.04 (d, J=8.0 Hz, 2H), 7.94 (d, J=8.0 Hz, 2H), 7.87 (s, 1H), 7.20 (d, J=8.0 Hz, 2H), 7.24 (d, J=8.0 Hz, 2H), 6.52 (dd, J=8.0, 4.0 Hz, 1H), 6.07 (dd, J=8.0, 4.0 Hz, 1H), 5.50 (s, 1H), 4.84 (d, J=12.0 Hz, 1H), 4.69 (d, J=12.0 Hz, 1H), 3.25-3.18 (m, 1H), 2.91-2.85 (m, 1H), 2.70 (s, 1H), 2.46 (s, 3H), 2.42 (s, 3H), 0.41 (s, 9H).

Step 2: Synthesis of (2R,3S,5R)-5-(6-amino-2-fluoro-9H-purin-9-yl)-2-ethynyl-2-(hydroxymethyl)tetrahydrofuran-3-ol (EFdA)

(2R,3S,5R)-2-ethynyl-5-(2-fluoro-6-((trimethylsilyl)amino)-9H-purin-9-yl)-2-(((4-methylbenzoyl)oxy)methyl)

tetrahydrofuran-3-yl 4-methylbenzoate (6.0 g, 9.97 mmol) was dissolved in THF (60 mL) and cooled to −25° C. Sodium methoxide in methanol (30 wt %; 1.80 g, 9.97 mmol) was slowly added, keeping the internal temperature below −20° C. The reaction mixture was stirred at −25° C. for 16 hours then quenched with acetic acid (1.14 mL, 19.94 mmol). The resulting solution was heated to 45° C. and concentrated to 60 mL. Water was added (0.90 g, 49.9 mmol) and the solvent was switched to ACN. The resulting slurry was concentrated to 50 mL, cooled to room temperature and aged for 30 minutes. The solid was collected by filtration, washed with ACN (3×30 mL) and water (2×6 mL), and dried to give (2R,3S,5R)-5-(6-amino-2-fluoro-9H-purin-9-yl)-2-ethynyl-2-(hydroxymethyl)tetrahydrofuran-3-ol (2.93 g). $^{1}$H-NMR: (600 MHz, d$_6$-DMSO, ppm): δ 8.29 (s, 1H), 7.82 (br s, 2H), 6.24 (dd, J=7.2, 5.0 Hz, 1H), 5.55 (d, J=5.5, 1H), 5.27 (dd, J=6.8, 5.7 Hz, 1H), 4.57 (m, 1H), 3.65 (dd, J=11.9, 5.7 Hz, 1H), 3.56 (dd, J=11.9, 6.8 Hz, 1H), 3.49 (s, 1H), 2.70 (m, 1H), 2.43 (m, 1H). $^{19}$F-NMR: (282 MHz, d$_6$-DMSO, ppm): LC-MS: (ES, m/z): 316.0818 [M+Na]$^+$.

Example 4

Synthesis of (2R,3S,5R)-5-(6-amino-2-fluoro-9H-purin-9-yl)-2-ethynyl-2-(hydroxymethyl)tetrahydrofuran-3-ol (EfdA) from (2R,3S)-2-Ethynyl-2-[4-methylbenzoyl)oxymethyl]-5-(pent-4-en-1-yloxy)tetrahydrofuran-3-yl 4-methylbenzoate

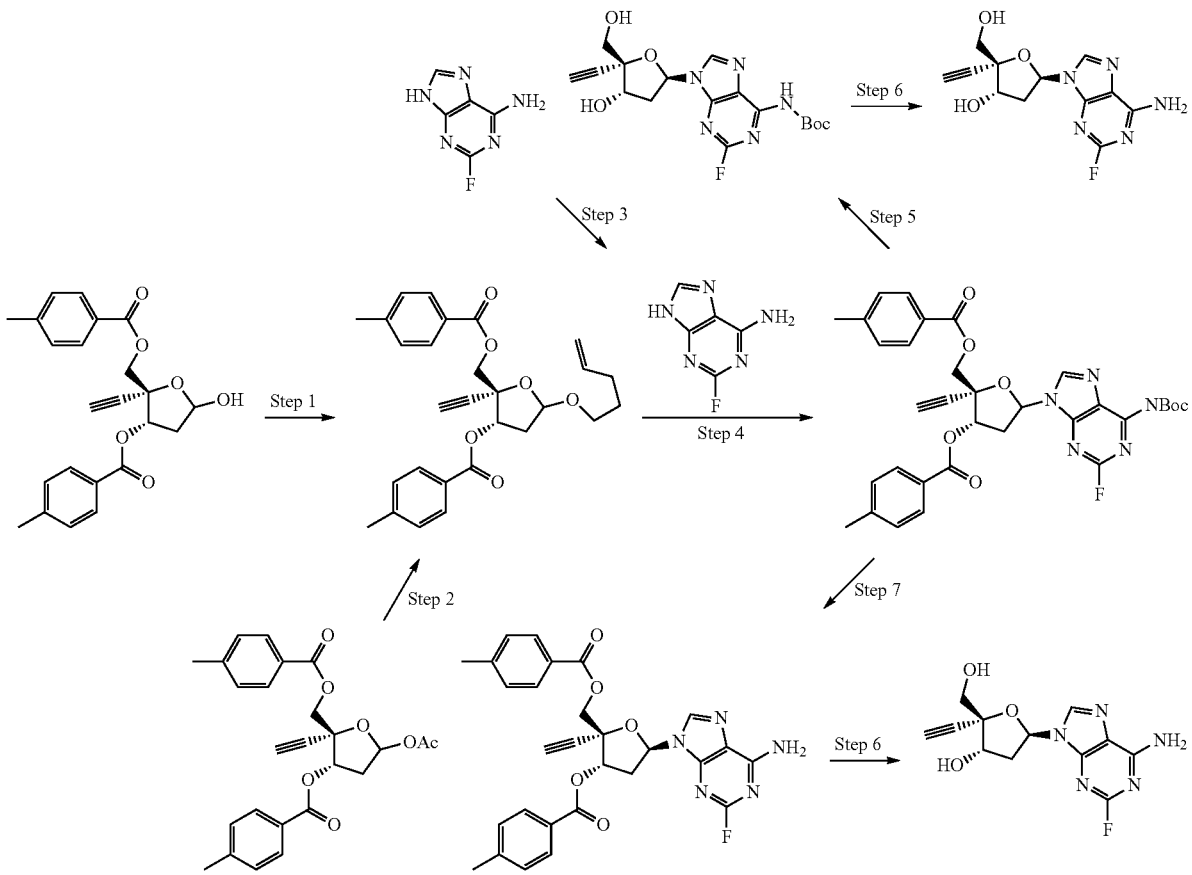

Step 1: Synthesis of (2R,3S)-2-Ethynyl-2-[4-methylbenzoyl)oxymethyl]-5-(pent-4-en-1-yloxy)tetrahydrofuran-3-yl 4-methylbenzoate To a stirred solution of p-toluenesulfonic acid monohydrate (0.76 g, 4 mmol) and 4-penten-1-ol (0.38 g, 4.4 mmol) in toluene (20 mL) at 0° C. was added (2R,3S)-2-ethynyl- 5-hydroxy-2-[(4-methylbenzoyl)oxymethyl]tetrahydrofuran-3-yl 4-methylbenzoate (11.15 wt % in toluene, 14.15 g, 4 mmol). The reaction mixture was stirred for 1 hour and quenched with water (30 mL). The organic layer was washed with saturated aqueous sodium bicarbonate (30 mL), water (30 mL) and saturated aqueous sodium chloride (30 mL). The resulting toluene solution was assayed by HPLC against a standard to give (2R,3S)-2-ethynyl-2-[4-methylbenzoyl) oxymethyl]-5-(pent-4-en-1-yloxy)tetrahydrofuran-3-yl 4-methylbenzoate, (1.6 g). HRMS (QTof) m/z: [M+Na]$^+$ calcd for $C_{28}H_{30}O_6Na$ 485.1940, found 485.1926.

Step 2: Synthesis of (2R,3S)-2-ethynyl-2-[4-methylbenzoyl)oxymethyl]-5-(pent-4-en-1-yloxy) tetrahydrofuran-3-yl 4-methylbenzoate To a stirred solution of (2R,3S)-5-acetoxy-2-ethynyl-2-(((4-methylbenzoyl)oxy)methyl)tetrahydrofuran-3-yl 4-methylbenzoate (2.0 g, 4.58 mmol) and 4-penten-1-ol (0.395 g, 4.58 mmol) in acetonitrile (20 mL) at 0° C. was added trimethylsilyl trifluoromethanesulfonate (0.083 ml, 0.458 mmol). The reaction mixture was stirred for 45 minutes and quenched with saturated sodium hydrogen carbonate solution (20 mL). The organic layer was washed 5% brine solution (20 mL), and the organics were concentrated to give (2R,3S)-2-ethynyl-2-[4-methylbenzoyl)oxymethyl]-5-(pent-4-en-1-yloxy)tetrahydrofuran-3-yl 4-methylbenzoate. (2R,3S)-2-ethynyl-2-[4-methylbenzoyl) oxymethyl]-5-(pent-4-en-1-yloxy) tetrahydrofuran-3-yl 4-methylbenzoate (2.1 g). $^1$H-NMR: (400 MHz, DMSO, ppm, mixture of anomers): δ 8.01-7.88 (m, 8H), 7.40-7.32 (m, 83), 5.92-5.58 (m, 4H), 5.40-5.27 (m, 2H), 5.09-4.87 (m, 4H), 4.64-4.35 (m, 4H), 3.78-3.32 (m, 6H), 2.70-2.41 (m, 4H), 2.40-2.35 (m, 12H), 2.20-2.12 (m, 2H), 2.04-1.93 (m, 2H), 1.69-1.61 (m, 2H), 1.56-1.42 (m, 2H).

Step 3: Synthesis of Tert-butyl (2-fluoro-9H-purin-6-yl)carbamate

To a stirred suspension of 2-fluoro-9H-purin-6-amine (20 g, 131 mmol) and 4-(dimethylamino)pyridine (1.6 g, 13 mmol) in THF (200 mL) at 0° C. was added di-tert-butyldicarbonate (100 g, 457 mmol) previously dissolved in THF (100 mL). The resulting suspension was stirred at 0° C. for 12 hours then diluted with MTBE (200 mL) and quenched with water (200 mL). The organic layer was washed with aqueous citric acid (10 wt %; 100 mL), water (2×100 mL) and saturated aqueous sodium chloride (100 mL). The resulting solution was then concentrated under reduced pressure to a 100 mL volume and diluted with ethanol (absolute, 400 mL). Aqueous sodium hydroxide (2.5 M, 313 mL, 784 mmol) was then added at 20° C. over 1 hour and the batch aged for 48 hours at this temperature. Solvents were distilled under reduced pressure and the aqueous solution was cooled to 0° C. and neutralized with hydrochloric acid (1N, 705 mL) to give a slurry. The solid was collected by filtration, washed with water (2×50 mL) and dried to give tert-butyl (2-fluoro-9H-purin-6-yl)carbamate (20 g, 79 mmol). 1H-NMR: (400 MHz, DMSO, ppm): δ 8.42 (s, 1H), 1.954 (s, 9H). HRMS (QTof) m/z: [M+H]$^+$ calcd for $C_{10}H_{13}FN_5O_2$ 254.1052, found 254.1053.

Step 4: Synthesis of (2R,3S,5R)-5-(6-((Tert-butoxycarbonyl)amino)-2-fluoro-9H-purin-9-yl)-2-ethynyl-2-(((4-methylbenzoyl)oxy)methyl)tetrahydrofuran-3-yl 4-methylbenzoate A dry stirred mixture of (2R,3S)-2-ethynyl-2-(((4-methylbenzoyl)oxy)methyl)-5-(pent-4-en-1-yloxy)tetrahydrofuran-3-yl 4-methylbenzoate (3.63 g, 7.85 mmol) and tert-butyl (2-fluoro-9H-purin-6-yl)carbamate (2.29 g, 9.04 mmol) in acetonitrile (80 mL) was cooled to −25° C. Iodine (6.30 g, 24.8 mmol) was added and the resulting mixture was stirred for 17 h, under a nitrogen atmosphere, at −25° C. The reaction mixture was then warmed to 0° C. and stirred at this temperature for a further 6 h. The reaction was quenched with aqueous sodium sulfite (10 wt %; 30 mL), diluted with water (40 mL), and then extracted with methyl tert-butyl ether (80 mL). The resulting organic layer was washed with aqueous sodium hydrogencarbonate (7 wt %; 40 mL) and then with aqueous sodium chloride (2 wt %; 42 mL). The organic layer obtained was concentrated to a volume of 35 mL, to form a slurry. To this stirred slurry, at ambient temperature, was slowly added water (12 mL). The resulting slurry was aged at ambient temperature and then filtered, washing the solid with 1:1 acetonitrile/water (2×10 mL). The resulting solid was dried to give (2R,3S,5R)-5-(6-((tert-butoxycarbonyl)amino)-2-fluoro-9H-purin-9-yl)-2-ethynyl-2-(((4-methylbenzoyl)oxy)methyl)tetrahydrofuran-3-yl 4-methylbenzoate (3.00 g). $^1$H-NMR: (400 MHz, CDCl$_3$, ppm): δ 8.06-8.02 (m, 4H), 7.92-7.89 (m, 2H), 7.33-7.29 (m, 2H), 7.26-7.22 (m, 2H), 6.56 (t, J=6.5 Hz, 1H), 6.08 (dd, J=7.2, 5.5 Hz, 1H), 4.89 (d, J=12.0 Hz, 1H), 4.67 (d, J=12.0 Hz, 1H), 3.24 (ddd, J=13.9, 7.4, 6.3 Hz, 1H), 2.95 (ddd, J=14.0, 6.9, 5.4 Hz, 1H), 2.73 (s, 1H), 2.47 (s, 3H), 2.43 (s, 3H), 1.59 (s, 9H). HRMS (QTof) m/z: [M+H]$^+$ calcd for $C_{33}H_{33}FN_5O_7$ 630.2364, found 630.2295.

Step 5: Synthesis of Tert-butyl (9-((2R,4S,5R)-5-ethynyl-4-hydroxy-5-(hydroxymethyl)tetrahydrofuran-2-yl)-2-fluoro-9H-purin-6-yl)carbamate A stirred solution of (2R,3S,5R)-5-(6-((tert-butoxycarbonyl)amino)-2-fluoro-9H-purin-9-yl)-2-ethynyl-2-(((4-methylbenzoyl)oxy)methyl)tetrahydrofuran-3-yl 4-methylbenzoate (1.5 g, 2.382 mmol) in a mixture of tetrahydrofuran (10 ml) and methanol (5 ml) was cooled to −20° C. Sodium methoxide (1.634 ml of a 25 wt % solution in methanol, 7.15 mmol) was added and the reaction was stirred for 4 h whilst monitoring the reaction progress by HPLC. The reaction was quenched by the addition of phosphoric acid (0.489 ml, 7.15 mmol) and the reaction was warmed to room temperature and the solid was filtered washing the cake with methanol. The filtrate was concentrated to provide tert-butyl (9-((2R,4S,5R)-5-ethynyl-4-hydroxy-5-(hydroxymethyl)tetrahydrofuran-2-yl)-2-fluoro-9H-purin-6-yl)carbamate, (0.47 g). $^1$H NMR (400 MHz, CDCl$_3$, ppm). 8.16 (s, 1H), 7.97 (s, 1H), 6.42-6.39 (dd, J=8.68, 5.78 Hz, 1H), 5.05-5.03 (m, 1H), 4.74-4.73 (m, 1H), 4.13-4.06 (m, 1H), 3.91-3.85 (m, 1H), 3.13-3.07 (m, 1H), 2.82 (S, 1H) 2.61 (bs, 1H), 2.54-2.50 (m, 1H), 1.57 (s, 9H) HRMS (QTof) m/z: [M+H]$^+$ calcd for $C_{17}H_{21}FN_5O_5$ 394.1527, found 394.1526.

Step 6: Synthesis of (2R,3S,5R)-5-(6-Amino-2-fluoro-9H-purin-9-yl)-2-ethynyl-2-(hydroxymethyl) tetrahydrofuran-3-ol (EFdA)

To a stirred solution of tert-butyl (9-((2R,4S,5R)-5-ethynyl-4-hydroxy-5-(hydroxymethyl)tetrahydrofuran-2-yl)-2-fluoro-9H-purin-6-yl)carbamate (0.05 g, 0.127 mmol) in dichloromethane (0.5 ml) was added trifluoroacetic acid (0.1 ml). The reaction mixture was aged at 20° C. for 16 h then concentrated to give (2R,3S,5R)-5-(6-amino-2-fluoro-9H-purin-9-yl)-2-ethynyl-2-(hydroxymethyl) tetrahydrofuran-3-ol (1), (0.012 g), which was confirmed by HPLC assay to a known standard.

Step 7: Synthesis of (2R,3S,5R)-5-(6-amino-2-fluoro-9H-purin-9-yl)-2-ethynyl-2-(((4-methylbenzoyl)oxy)methyl) tetrahydrofuran-3-yl 4-methylbenzoate To a stirred solution of (2R,3S,5R)-5-(6-((tert-butoxycarbonyl)amino)-2-fluoro-9H-purin-9-yl)-2-ethynyl-2-(((4-methylbenzoyl)oxy)methyl)tetrahydrofuran-3-yl 4-methylbenzoate (0.5 g, 0.794 mmol) in toluene (5 ml) at 20° C., was added trifluro acetic acid (0.5 ml). The reaction was aged for 24 h whilst monitoring the reaction progress by HPLC. The reaction was quenched by the addition of saturated sodium hydrogen carbonate (10 ml) and ethyl acetate was added (10 ml). The organics were washed with water (10 ml) and concentrated to give (2R,3S,5R)-5-(6-amino-2-fluoro-9H-purin-9-yl)-2-ethynyl-2-(((4-methylbenzoyl)oxy)methyl) tetrahydrofuran-3-yl 4-methylbenzoate (0.40 g). 1H NMR (400 MHz, CDCl$_3$, ppm). 8.3-8.1 (d, J=8.29 Hz, 2H), 7.93-7.91 (d, J=8.29 Hz, 2H), 7.89 (s, 1H), 7.30-7.28 (d, J=8.29 Hz, 2H), 7.23-7.21 (d, J=8.29 Hz, 2H), 6.52-6.49 (t, J=6.68 Hz, 1H), 6.07-6.04 (dd, J=7.22, 5.35 Hz, 1H), 5.89 (bs, 2H), 4.86-4.83 (d, J=11.76 Hz, 1H), 4.67-4.64 (d, J=11.76 Hz, 1H), 3.22-3.18 (m, 1H), 2.90-2.87 (m, 1H), 2.69 (s, 1H), 2.45 (s, 3H). 2.44-2.43 (m, 1H), 2.45 (s, 1H). HRMS (QTof) m/z: [M+H]$^+$ calcd for C$_{28}$H$_{25}$FN$_5$O$_5$ 530.1840, found 530.1885.

Step 8: Synthesis of (2R,3S,5R)-5-(6-amino-2-fluoro-9H-purin-9-yl)-2-ethynyl-2-(hydroxymethyl) tetrahydrofuran-3-ol (EfdA)

A stirred solution (2R,3S,5R)-5-(6-amino-2-fluoro-9H-purin-9-yl)-2-ethynyl-2-(((4-methylbenzoyl)oxy)methyl) tetrahydrofuran-3-yl 4-methylbenzoate (0.084 g, 0.159 mmol) in a mixture of tetrahydrofuran (0.84 ml) and methanol (0.42 ml) was cooled to −20° C. Sodium methoxide (0.109 ml of a 25 wt % solution in methanol, 0.476 mmol) was added and the reaction was stirred for 16 h whilst monitoring the reaction progress by HPLC. The reaction was quenched by the addition of phosphoric acid (0.47 g, 0.476 mmol) and the reaction was warmed to room temperature and the solid was filtered washing the cake with methanol. The filtrate was concentrated to give (2R,3S,5R)-5-(6-amino-2-fluoro-9H-purin-9-yl)-2-ethynyl-2-(hydroxymethyl) tetrahydrofuran-3-ol (EfdA), (0.039 g), which was confirmed by HPLC assay to a known standard.

RT Polymerase Assay

Full-length wild-type and 2 mutant RT proteins were expressed in Escherichia coli BL21(DE3) cells and purified. Briefly, the heterodimeric nucleic acid substrate used in the HIV-1 RT polymerase reactions was generated by annealing biotinylated DNA primer to a 500 nucleotide RNA template. The HIV-1 RT enzyme (final concentration of 50 pM) was combined with an inhibitor compound or DMSO (10% DMSO in the final reaction mixture) in assay buffer (62.5 mM Tris-HCl, pH 7.8, 1.25 mM dithiothreitol, 7.5 mM MgCl$_2$, 100 mM KCl, 0.03% CHAPS, 0.125 mM EGTA). This mixture was pre-incubated for 30 minutes at room temperature in microtiter plates. The polymerization reaction was initiated by the addition of template/primer substrate (final concentration: 16.6 nM) and dNTPs (final concentration: 2 μM dCTP, dGTP, dATP, and 66.6 nM Ru-dUTP). After 90 min of incubation at 37° C., reactions were quenched by the addition of EDTA (25 mM). The resulting mixture was incubated for an additional 5 minutes at room temperature followed by transferring the solution (50 μL) to blocked avidin plate from Meso Scale Discovery (MSD). The mixtures were incubated at room temperature for 60 min prior to the quantification of the reaction product via an ECL 6000 imager instrument. The resulting data is shown in Table 1.

TABLE 1

| Example No. | Structure | dNTP IC$_{50}$ (nM) |
|---|---|---|
| 2 | (chemical structure: triphosphate nucleoside analog with 4 NH$_4^+$ counterions; 2-ethynyl, 3-hydroxy tetrahydrofuran linked to 5-fluoro-2-chloro-4-amino-7H-pyrrolo[2,3-d]pyrimidine) | 490 |

Viking Assay:

Assessing antiviral potency in a multiple round HIV-1 infection assay. HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection.

MT4-GFP cells were maintained at 37° C./5% CO$_2$/90% relative humidity in RPMI 1640 supplemented with 10% fetal bovine serum, 100 U/mL penicillin/streptomycin, and 400 μg/mL G418 to maintain the reporter gene. For infections, MT4-GFP cells were placed in the same medium lacking G418 and infected overnight with H9IIIB virus at an approximate multiplicity of infection of 0.01 in the same incubation conditions. Cells were then washed and re-suspended in either RPMI 1640 containing 10% or 50% normal human serum at 1.6×10$^5$ cells/mL (10% or 50% NHS conditions) or in 100% normal human serum at 2×10$^5$ cells/mL (100% NHS conditions). Compound plates were prepared by dispensing compounds dissolved in DMSO into wells of 384 well poly D lysine-coated plates (0.2 μl/well) using an ECHO acoustic dispenser. Each compound was tested in a 10 point serial 3-fold dilution (typical final concentrations: 8.4 μM-0.43 nM). Controls included no inhibitor (DMSO only) and a combination of three antiviral agents (efavirenz, indinavir, and an integrase strand transfer inhibitor at final concentrations of 4 µM each). Cells were added (50 µL/well) to compound plates and the infected cells were maintained at 37° C./5% $CO_2$/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, $R_0$, which is typically 5-15 and has been shown experimentally to be in logarithmic phase (data not shown). Inhibition of $R_0$ is calculated for each well, and $EC_{50}$s determined by non-linear 4-parameter curve fitting.

CTG Assay:
Assessing cytotoxicity in CellTiter-Glo Luminescent Cell Viability assay (CTG).

MT4-GFP cells were seeded in RPMI 1640 supplemented with 10% fetal bovine serum, 100 U/mL penicillin/streptomycin overnight at 37° C./5% $CO_2$/90% relative humidity. Cells were then washed and resuspended in RPMI 1640 containing 10% normal human serum at a density of $0.8 \times 10^5$ cells/mL. Compound plates were prepared by dispensing compounds dissolved in DMSO into wells of 384 well solid black plates (Corning 3571) using an ECHO acoustic dispenser (0.2 µl/well). Each compound was tested in a 10 point serial 3-fold dilution (final concentrations: 8.4 µM-0.43 nM). Controls included DMSO. Cells were added (50 µL/well) to compound plates and were maintained at 37° C./5% $CO_2$/90% relative humidity. CTG reagent (Promega, G7573) was added to the cell plates after 48 h incubation according to the manufacturer's description. Luminescence signals were recorded on EnVision plate reader (PerkinElmer). $LD_{50}$s were determined by non-linear 4-parameter curve fitting. The resulting data is shown in Table 2 with the marketed HIV nucleoside reverse transcriptase inhibitor AZT (azidothymidine, zidovudine) included as a control.

TABLE 2

| Structure | Viking, $EC_{50}$ (10% NHS) (nM) | CTG (µM) |
|---|---|---|
| AZT | 37 | >8.4 |

| Example No. | Structure | Viking, $EC_{50}$ (10% NHS) (nM) | CTG (µM) |
|---|---|---|---|
| 1 | 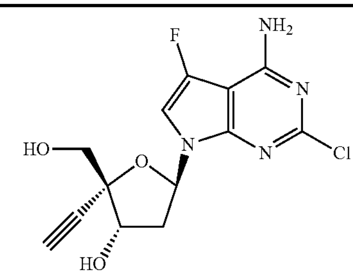 | 1.2 | >8.4 |

Antiviral Persistence in Human Peripheral Blood Mononuclear Cells (PBMC)

PBMCs were obtained from Biological Specialty Corporation, activated with 5 µg/ml PHA-P (Sigma L1668) for 72 hrs, and then washed with fresh medium. Following activation, PBMCs were cultured in media containing 10 IU/ml IL-2 (Roche 11011456001). Cells were treated with a titration of compound for 6 or 24 hrs and washed with fresh medium. To evaluate persistence of antiviral activity following wash-out, PBMCs were maintained for either 24 h or 72 h and then infected by adding wild-type HIV-1-GFP virus (17 µL/well) to the plates and incubating at 37° C./5% $CO_2$/90% relative humidity. Infected cells were quantified at 24 h post-infection by counting the number of green cells in each well using an Acumen eX3 scanner. EC50 values in Table 3 were calculated by non-linear 4-parameter curve fitting.

The antiviral persistence assay is meant to assess for the persistence of antiviral activity upon removal of the nucleoside. The data in Table 3 demonstrates the antiviral persistence of compounds of this invention in comparison to marketed nucleoside AZT. The publication *AIDS Research and Therapy*, 2009, 6:5, highlights the value of antiviral persistence.

TABLE 3

| | Structure | $EC_{50}$ 24 h (nM) | $EC_{50}$ 72 h (nM) |
|---|---|---|---|
| AZT | 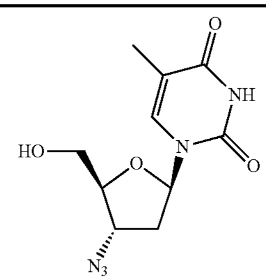 | 19 | 68 |

| Example No. | Structure | $EC_{50}$ 24 h (nM) | $EC_{50}$ 72 h (nM) |
|---|---|---|---|
| 1 | | 0.38 | 3.8 |

Adenosine Deaminase (ADA) Half-Life

The data in Table 4 was generated by testing the reactivity of the substrate compound with human ADA type 1 in the presence of Tris-HCl buffer (pH 7.5) at 40° C. and monitoring by LCMS for consumption of starting material. The time necessary for 50% conversion to the corresponding inosine product is noted as the $T_{1/2}$ in Table 4. It is known that deamination by adenosine deaminase decreases the therapeutic potential of adenosine-like nucleoside inhibitors especially in vivo (see references below). The compounds shown in Table 4 have been shown to have varying degrees of stability to adenosine deaminase when compared to EDA ((2R,3S,5R)-5-(6-amino-9H-purin-9-yl)-2-ethynyl-2-(hydroxymethyl)tetrahydrofuran-3-ol) and natural deoxyadenosine. It is possible that compounds that are more resistant to ADA will have better pharmacokinetic properties.

REFERENCES

Journal of Medicinal Chemistry 1996, 39, 19, 3847; Chemical Pharmaceutical Bulletin. 1994, 42, 8, 1688-1690; Antimicrobial Agents and Chemotherapy (2013), 57(12), 6254-6264; Collection of Czechoslovak Chemical Communications (2006), 71(6), 769-787; Microbiologica (1995), 18(4), 359-70; J Antivir Antiretrovir S10.doi: 10.4172/jaa.S10-002.

While the foregoing specification teaches the principles of the present invention, with examples provided for the purpose of illustration, the practice of the invention encompasses all of the usual variations, adaptations and/or modifications that come within the scope of the following claims. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All publications, patents and patent applications cited herein are incorporated by reference in their entirety into the disclosure.

TABLE 4

| | Structure (Substrate) | Inosine Product | $T_{1/2}$ |
|---|---|---|---|
| Deoxyadenosine | [structure] | [structure] | <10 min |
| EDA | [structure] | [structure] | <60 min |

| Example No | Structure (Substrate) | Inosine Product | $T_{1/2}$ |
|---|---|---|---|
| 1 | [structure] | [structure] | NA |

NA: Substrate insensitive to Adenosine Deaminase. 100% of the substrate was seen after 10 days of incubation with ADA.

What is claimed:

1. A compound of structural Formula I

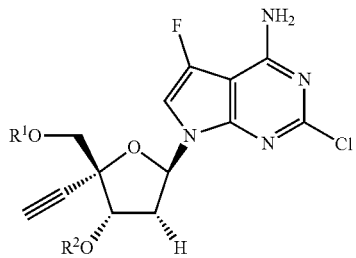

or a pharmaceutically acceptable salt thereof, wherein:
$R^1$ is —H, —C(O)$R^3$, —C(O)O$R^3$, —C(O)N($R^3$)$_2$,

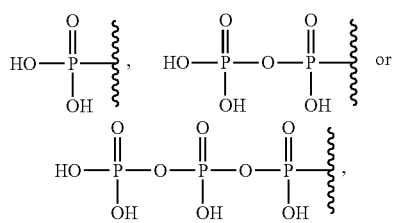

or a pro-drug modification of the mono-, di- or triphosphate; and
$R^2$ is —H, —C(O)$R^4$, —C(O)O$R^4$ or —C(O)N($R^4$)$_2$;
$R^3$ and $R^4$ are each independently selected at each occurrence from —H, —$C_1$-$C_6$ alkyl, —$C_1$-$C_6$ haloalkyl, —($C_1$-$C_3$ alkylene)$_m$-($C_3$-$C_7$ cycloalkyl), —($C_1$-$C_3$ alkylene)$_m$-(aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein each of said —$C_1$-$C_6$ alkyl, said —$C_3$-$C_7$ cycloalkyl group, said aryl group, said 4 to 7-membered heterocycloalkyl group, said 5- or 6-membered monocyclic heteroaryl group or said 9- or 10-membered bicyclic heteroaryl group is unsubstituted or substituted with $R^5$;
m is an integer selected from 0 (zero) or 1; and
$R^5$ represents from one to five substituent groups, each independently selected from —$C_1$-$C_6$alkyl, —$C_2$-$C_6$ alkenyl, —$C_2$-$C_6$ alkynyl, —$C_1$-$C_6$ haloalkyl, aryl or a 5-6-member heteroaryl.

2. The compound of claim 1 or a pharmaceutically acceptable salt thereof wherein $R^1$ is —H, —C(O)$R^3$, —C(O)O$R^3$, —C(O)N($R^3$)$_2$, or a pro-drug modification of one of the following mono-, di- or triphosphate moieties:

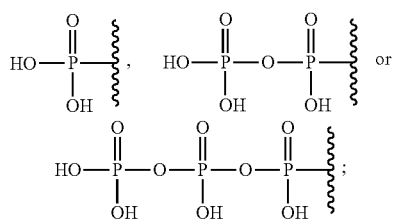

and
$R^2$ is —H, —C(O)$R^4$, —C(O)O$R^4$ or —C(O)N($R^4$)$_2$.

3. The compound of claim 1 or a pharmaceutically acceptable salt thereof wherein $R^1$ is —H, —C(O)$R^3$, —C(O)O$R^3$, or —C(O)N($R^3$)$_2$; and $R^2$ is —H, —C(O)$R^4$, —C(O)O$R^4$ or —C(O)N($R^4$)$_2$.

4. The compound of claim 1 or a pharmaceutically acceptable salt thereof wherein $R^1$ is

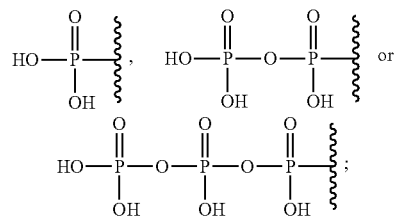

and $R^2$ is —H.

5. The compound of claim 1 that is

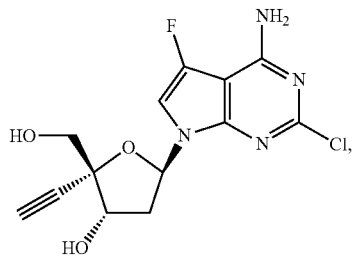 [SMILES: C#C[C@]1(CO)O[C@@H](n2cc(F)c3c(N)nc(Cl)nc32)C[C@@H]1O]

or a pharmaceutically acceptable salt thereof.

6. The compound of claim 1 that is

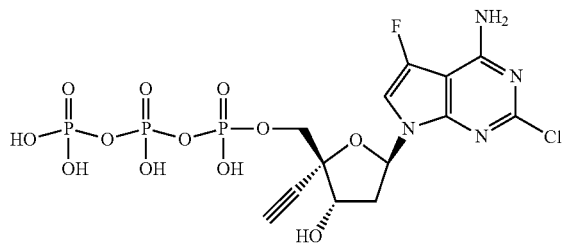 [SMILES: C#C[C@]1(COP(=O)(O)OP(=O)(O)OP(=O)(O)O)O[C@@H](n2cc(F)c3c(N)nc(Cl)nc32)C[C@@H]1O]

or a pharmaceutically acceptable salt thereof.

7. A pharmaceutical composition comprising the compound of claim 1 or a pharmaceutically acceptable salt thereof, and a pharmaceutically acceptable carrier.

8. A pharmaceutical composition comprising the compound of claim 1, or a pharmaceutically acceptable salt thereof, and a pharmaceutically acceptable carrier and further comprising one or more anti-HIV agents selected from HIV antiviral agents, immunomodulators, and anti-infective agents.

9. The pharmaceutical composition of claim 8, wherein the HIV antiviral agent is selected from one or more of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

10. A method for the treatment of infection by HIV or for the treatment or delay in the onset of AIDS in a subject in need thereof, which comprises administering to the subject the compound of claim 1 or a pharmaceutically acceptable salt thereof.

11. The method of claim 10 further comprising administering to the subject one or more additional HIV antiviral agents selected from HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

12. The method of claim 10 further comprising administering to the subject one or more additional HIV antiviral agents selected from: abacavir, abacavir sulfate, abacavir+lamivudine, abacavir+lamivudine+zidovudine, amprenavir, atazanavir, atazanavir sulfate, AZT, capravirine, darunavir, dideoxycytidine, dideoxyinosine, delavirdine, delavirdine mesylate, dolutegravir, doravirine, efavirenz, efavirenz+emtricitabine+tenofovir disoproxil fumarate, 4'-ethynyl-2-fluoro-2'-deoxyadenosine, elvitegravir, emtricitabine, emtricitabine+tenofovir disoproxil fumarate, emivirine, enfuvirtide, etravirine, fosamprenavir calcium, indinavir, indinavir sulfate, lamivudine, lamivudine+zidovudine, lopinavir, lopinavir+ritonavir, maraviroc, nelfinavir, nelfinavir mesylate, nevirapine, PPL-100, raltegravir, rilpivirine, ritonavir, saquinavir, saquinavir mesylate, stavudine, tenofovir disoproxil fumarate, tenofovir alafenamide fumarate, tipranavir, or vicriviroc.

* * * * *